US008309568B2

(12) United States Patent
Stinchcomb et al.

(10) Patent No.: US 8,309,568 B2
(45) Date of Patent: *Nov. 13, 2012

(54) TRANSDERMALLY DELIVERABLE OPIOID PRODRUGS, ABUSE-RESISTANT COMPOSITIONS AND METHODS OF USING OPIOID PRODRUGS

(75) Inventors: Audra Lynn Stinchcomb, Lexington, KY (US); Miroslaw Jerzy Golinski, Lexington, KY (US); Dana Carmel Hammell, Georgetown, KY (US); Jeffrey Lynn Howard, Richmond, KY (US)

(73) Assignee: Alltranz Inc., Lexington, KY (US)

( * ) Notice: Subject to any disclaimer, the term of this patent is extended or adjusted under 35 U.S.C. 154(b) by 64 days.

This patent is subject to a terminal disclaimer.

(21) Appl. No.: 12/388,891

(22) Filed: Feb. 19, 2009

(65) Prior Publication Data

US 2009/0156814 A1 Jun. 18, 2009

Related U.S. Application Data

(63) Continuation of application No. 11/860,432, filed on Sep. 24, 2007, now Pat. No. 7,511,054.

(60) Provisional application No. 60/826,603, filed on Sep. 22, 2006.

(51) Int. Cl.
*A61K 31/4748* (2006.01)
*C07D 491/08* (2006.01)

(52) U.S. Cl. .......................................... 514/279; 546/39
(58) Field of Classification Search .................... 546/39, 546/38; 514/279
See application file for complete search history.

(56) References Cited

U.S. PATENT DOCUMENTS 7,084,150 B2 * 8/2006 Boer et al. ..................... 514/279
7,511,054 B2 * 3/2009 Stinchcomb et al. ......... 514/279

OTHER PUBLICATIONS

Abraham, Michael, "Application of solvation equations to chemical and biochemical processes," Pure & Appl. Chem., vol. 65 (12), pp. 2503-2512 (1993).
Agarwal, et al., "Studies on Polynucleotides. CII. The Use of Aromatic Isocyanates for Selective Blocking of the Terminal 3'-Hydroxyl Group in Protected Deoyribooligonucleotides," Journal of the American Chemical Society, vol. 94 (10), pp. 3578-3585 (1972).
Anderson, et al., "Enhanced Oral Bioavailibility of DDI after Administration of 6-C1-ddP, an Adenosine Deaminase-Activated Prodrug, to Chronically Catheterized Rats," Pharmaceutical Research, vol. 12(8), pp. 1126-1133 (1995).
Anderson, Bradley D., "Prodrugs for improved CNS delivery," Advanced Drug Delivery Reviews, vol. 19, pp. 171-202 (1996).
Ando, et al., "Skin as an active metabolizing barrier I: Theoretical anaylsis of topical bioavailability," Journal of Pharmaceutical Sciences, vol. 66(11), pp. 1525-1528 (1977).
Anton, et al., "Naltrexone and Cognitive Behavorial Therapy for the Treatment of Outpatient Alcoholics: Results of a Placebo-Controlled Trial," Am J Psychiatry, vol. 156(11), pp. 1758-1764 (1999).
Avison, A.W.D., "The Application of Lithium Aluminium Hydride to the Preparation of some Amino-Alkanols," J. appl. Chem., vol. 1(10), pp. 469-472 (1951).
Blumberg, et al., "Comparison of naltrexone and beta-naltrexol for narcotic antagonist action in rats and mice," Federation Proceedings, vol. 35, p. 469, No. 1453 (1976).
Bradford, Marion M., "A Rapid and Sensitive Method for the Quantitation of Microgram Quantities of Protein Utilizing the Principle of Protein-Dye Binding," Analytical Biochemistry, vol. 72, pp. 248-254 (1976).
Brewer, Colin, "Serum naltrexone and 6-beta-naltrexol levels from naltrexone implants can block very large amounts of heroin: a report of two cases," Addiction Biology, vol. 7, pp. 321-323 (2002).
Bullington, et al., "Clinical pharmacokinetics of narcotic agonist-antagonist drugs," Clinical Pharmacokinetics, vol. 8, pp. 332-343 (1983).
Chiang, et al., "Clinical evaluation of a naltrexone sustained-release preparation," Drug and Alcohol Dependence, vol. 16, pp. 1-8 (1985).
Chiang, Nora C. and Finnegan, Loretta P., editors, "Medications Development for the Treatment of Pregnant Addicts and Their Infants," NIDA Research Monograph Series, vol. 149, pp. 1-246 (1995).
Chou, et al., "Determination of nalmefene in plasma by high-performance liquid chromatography with electrochemical detection and its application in pharmacokinetic studies," Journal of Chromatography, vol. 613, pp. 359-364 (1993).
Ciccocioppo, et al., "Ethanol iduces conditioned place preference in genetically selected alcohol-preferring rats," Psychopharmacology, vol. 141, pp. 235-241 (1999).
Ciccocioppo, et al., "Buprenorphine Reduces Alcohol Drinking Through Activation of the Nociceptin/Orphanin FQ-NOP Receptor System," Biol. Psychiatry, vol. 61, pp. 4-12 (2007).
Cippitelli, et al., "The anandamide transport inhibitor AM404 reduces ethanol self-administration," European Journal of Neuroscience, vol. 26, pp. 476-486 (2007).
Cohen, et al., "Chronic Intraveneous Hyperalimentation in the Neonatal Pigley," Swine in Biomedical Research, vol. 2, pp. 1265-1275, Plenum Press, New York (1986).
Comer, et al., "Depot naltrexone: long-lasting antagonism of the effects of heroin in humans," Psychopharmacology, vol. 159, pp. 351-360 (2002).
Cone, et al., "The urinary excretion profile of naltrexone and metabolites in man," Drug Metabolism and Disposition, vol. 2(6), pp. 506-512 (1974).
Crotti, et al., "Aminolysis of Oxetanes: Quite Efficient Catalysis by Lanthanide (III) Trifluoromethansulfonates," Tetrahedron Letters, vol. 35(38), pp. 7089-7092 (1994).
Curdy, et al., "Non-invasive assessment of the effects of iontophoresis on human skin in-vivo," Journal of Pharmacy and Pharmacology, vol. 53, pp. 769-777 (2001).
Davidson, et al., "Determination of naltrexone and its major metabolite, 6-β-naltrexol, in human plasma using liquid chromatography with electrochemical detection," Journal of Pharmaceutical and Biomedical Analysis, vol. 14, pp. 1717-1725 (1996).

(Continued)

*Primary Examiner* — Charanjit Aulakh
(74) *Attorney, Agent, or Firm* — Foley & Lardner LLP

(57) ABSTRACT

Described herein are opioid prodrugs, methods of making opioid prodrugs, formulations comprising opioid prodrugs, and methods of using opioid prodrugs. One embodiment described herein relates to the transdermal administration of a buprenorphine prodrug in an abuse-resistant formulation for treating and preventing diseases and/or disorders.

18 Claims, 6 Drawing Sheets

OTHER PUBLICATIONS

Davidson, et al., "Effects of Naltrexone on Alcohol Self-Administration in Heavy Drinkers," Alcohol Clin Exp. Res, vol. 23(2), pp. 195-203 (1999).

Davis, et al., "Isothiocyanate-Substituted Benzyl Ether Opiod Receptor Ligands Derived from 6β-Naltrexol," J. Med. Chem, vol. 38, pp. 570-579 (1995).

Davis, et al., "Insertion of microneedles into skin: measurement and prediction of insertion force and needle fracture force," Journal of Biomechanics, vol. 37, pp. 1155-1163 (2004).

Dayton, et al., "The urinary excretion profiles of naltrexone in man, monkey, rabbit, and rat," Drug Metabolism and Disposition, vol. 4(5), pp. 474-478 (1976).

Drobes, et al., "Effects of Naltrexone and Nalmefene on Subjective Response to Alcohol Among Non-Treatment-Seeking Alcoholics and Social Drinkers," Alcohol Clin Exp Res, vol. 28(9), pp. 1362-1370 (2004).

Drustrup, et al., "Utilization of prodrugs to enhance the transdermal absorption of morphine," International Journal of Pharmaceutics, vol. 71, pp. 105-116 (1991).

El Tayar, et al., "Percutaneous Penetration of Drugs: A Quantitative Structure-Permeability Relationship Study," Journal of Pharmaceutical Sciences, vol. 80(8), pp. 744-749 (1991).

Elkader, et al., "Buprenorphine: Clinical Pharmacokinetics in the Treatment of Opiod Dependence," Clin Pharmacokinet, vol. 44(7), pp. 661-680 (2005).

Ferguson, et al., "Burn wound evaporation—measurement of body fluid loss by probe evaporimeter and weight change," Clin. Phys. Physiol Meas., vol. 12(2), pp. 143-155 (1991).

Ferrari, et al., "Serum time course of naltrexone and 6β-naltrexol levels during long term treatment in drug addicts," Drug and Alcohol Dependence, vol. 52, pp. 211-220 (1998).

Finnen, et al., "Distribution and subcellular localization of drug metabolizing enzymes in the skin," British Journal of Dermatology, vol. 113, pp. 713-721 (1985).

Flynn, Gordon L., "Physicochemical Determinants of Skin Absorption," Principles of Route-to-Route Extrapolation of Risk Assessment, T.R. Gerruty and C.J. Henry, editors, pp. 93-127 (1990).

Fujimoto, et al., "Narcotic antagonist activity of several metabolites of naloxone and naltrexone tested in morphine dependent mice," Proceedings of the Society for Experimental Biology and Medicine, vol. 148, pp. 443-448 (1975).

Garbutt, et al., "Efficacy and Tolerability of Long-Acting Injectable Naltrexone for Alcohol Dependence: A Randomized Controlled Trial," JAMA, vol. 293(13), pp. 1617-1625 (2005), corrected in JAMA, vol. 293(16), p. 1978 (2005) and JAMA, vol. 293(23), p. 2864. (2005).

Garrett, et al., "Pharmacokinetics of morphine and its surrogates V: Naltrexone and naltrexone conjugate pharmacokinetics in the dog as a function of dose," Journal of Pharmaceutical Sciences vol. 74(1), pp. 50-56, (1985).

Gerstein, Dean R and Harwood, Henrick J., editors., "Treating Drug Problems: A Study of the Evolution, Effectiveness, and Financing of Public and Private Drug Treatment Systems," National Academy Press, vol. 1, pp. 1-332 (1990).

Gibaldi, "Consecutive Constant Rate Intravenous Infusions," Pharmacokinetics, pp. 75-81, Marcel Dekker, Inc. New York (1982).

Grandin, et al., "Effect of Naltrexone on Relaxation Induced by Flank Pressure in Pigs," Pharmacology Biochemistry & Behavior vol. 33, pp. 839-842 (1989).

Gresham, et al., "β-Propiolactone V. Reaction with Alcohols", J. Am. Chem. Soc., vol. 70(3), pp. 1004-1006 (1948).

Hammell, et al., "A duplex "Gemini" prodrug of naltrexone for transermal delivery," Journal of Controlled Release, vol. 97, pp. 283-290 (2004).

Hansen,et al., "Carbamate Ester Prodrugs of Dopaminergic Compounds: Synthesis, Stability and Bioconversion," Journal of Pharmaceutical Sciences, vol. 80(8), pp. 793-798, (1991).

Hennink, et al., "Novel crosslinking methods to design hydrogels," Advanced Drug Delivery Reviews, vol. 54, pp. 13-36, (2002).

Henry, et al., "Microfabricated Microneedles: A Novel Approach to Transdermal Drug Delivery," Journal of Pharmaceutcal Sciences, vol. 87(8), pp. 922-925, (1998).

Hood, et al, "The Effects of an Alpha Hydroxy Acid (Glycolic Acid) on Hairless Guinea Pig Skin Permeabiilty," Food and Chemical Toxicology, vol. 37, pp. 1105-1111, (1999).

Hussain, et al., "Improvement of the Oral Bioavailability of Naltrexone in Dogs: A Prodrug Approach," Journal of Pharmaceutical Sciences vol. 76(5), pp. 356-358, (1987).

Hussain, et al., "Improved Buccal Delivery of Opioid Analgesics and Antagonists with Bltterlesss Prodrugs," Pharmaceutical Research, vol. 5(9), pp. 615-618, (1988).

Johnson, et al., "A Pilot Evaluation of the Safety and Tolerability of Repeat Dose Administration of Long-Acting Injectable Naltrexone (Vivitrex®) in Patients with Alcohol Dependence," Alcohol Clin Exp Res, vol. 28(9), pp. 1356-1361 (2004).

Johnson, et al., "Buprenorphine: Considerations for Pain Management," Journal of Pain and Symptom Management, vol. 29(3), pp. 297-326, (2005).

Kalia, et al., "Heterogeneous Transport in a Heterogeneous Membrane: Water Diffusion Across Human Stratum Corneum In Vivo," Biophysical Journal, vol. 71, pp. 2692-2700 (1996).

Kaushik, et al., "Lack of Pain Associated with Microfabricated Microneedles," Anesth Analg,vol. 92, pp. 502-504, (2001).

Kintz, P., "Deaths involving buprenorphine: a compendium of French cases," Forensic Sciences International, vol. 121, pp. 65-69 (2001).

Kranzler, et al., "Sustained-Release Naltrexone for Alcoholism Treatment: A Preliminary Study," Alcohol Clin Exp Res, vol. 22(5), pp. 1074-1079 (1998).

Kranzler, et al., "Naltrexone Depot for Treatment of Alcohol Dependence: A multicenter, Randomized, Placebo-Controlled Clinical Trial," Alcohol Clin Exp Res, vol. 28(7), pp. 1051-1059 (2004).

Lamontagne, et al., "Analogues of 8-[[6-(Diethylamino)hexyl]amino]-6-methoxy-4-methylquinoline as Candidate Antileishmanial Agents," J. Med Chem. vol. 23, 981-985,(1980).

Lewis, J.W., "Buprenorphine," Drug and Alcohol Dependence, vol. 14, pp. 363-372 (1985).

Lien, et al., "QSAR Analysis of Skin Permeability of Various Drugs in Man as Compared to in Vivo and in Vitro Studies in Rodents," Pharmaceutical Research, vol. 12(4), pp. 583-587 (1995).

Litten, et al., "Advances in development of medications for alcoholism treatment," Psychopharmalcology , vol. 139, pp. 20-33 (1998).

Licko, Vojtech, "Overview of Human Pharmacokinetics of Naltrexone," Naltrexone: Research Monograph 28, Willett, R.E. and Barnett, G., editors, pp. 161-171, (1980).

Lunney, et al., "A Novel Nonpeptide HIV-Protease Inhibitor: Elucidation of the Binding Mode and its Application in the Design of Related Analogs," J. Med. Chem., vol. 37, pp. 2664-2677 (1994).

Malspeis, et al., "Metabolic reduction of naltrexone I. Synthesis, separation and characterization of naloxone and naltrexone reduction products and qualitative assay of urine and bile following adminstration fo naltrexone, α-natrexol, or β-naltrexol," Research Communicaitons in Chemical Pathology and Pharmacology, vol. 12(1), pp. 43-65 (1975).

Martanto, et al., "Transdermal Delivery of Insulin Using Microneedles in Vivo," Pharmaceutical Research, vol. 21(6), pp. 947-952 (2004).

Martin, et al., "Diagnosis and Assessment of Alcohol Use Disorders Among Adolescents," Alcohol Health and Research World, vol. 22(2), pp. 95-106 (1998).

McAllister, et al., "Microfabricated needles for transdermal delivery of macromolecules and nanoparticles: Fabrication methods and transport studies," PNAS, vol. 100(24), pp. 13755-13760 (2003).

McCaul, et al., "β-Natrexol Level Predicts Alcohol Relapse," RSA Abstracts, No. 172, p. 32A (1997).

McCaul, et al., "Serum 6-Beta-Naltrexol Levels are Related to Alcohol Responses in Heavy Drinkers," Alcohol Clin Exp Res, vol. 24(9), pp. 1385-1391 (2000).

Meyer, et al., "Bioequivalence, dose-proportionality and pharmacokinetics of naltrexone after oral administration," Journal of Clinical Psychiatry, vol. 45(9), pp. 15-19 (1984).

Moon, et al., "Diseased Skin Models in the Hairless Guinea Pig: in vivo Percutaneous Absorption," Dermatologica, vol. 180, pp. 8-12 (1990).

Morgan, et al., "Central Nervous System Targeting of 2',3'-Dideoxyinosine via Adenosine Deaminase-Activated 6-Halo-Dideoxypurine Prodrugs," Antimcrobial Agents and Chemotherapy, vol. 36(10), pp. 2156-2165 (1992).

Olsen, et al., "A Review of Parenteral Sustained-Release Naltrexone Systems," Naltrexone: Research Monograph 28, Willett, R.E. and Barnett, G., editors, pp. 187-193, (1980).

O'Malley, et al., "Naltrexone and Coping Skills Therapy for Alcohol Dependence," Arch Gen Psychiatry, vol. 49, pp. 881-887 (1992).

Oncken, et al., "Adverse effects of oral naltrexone: analysis of data from two clinical trials," Psychopharmacology, vol. 154, pp. 397-402 (2001).

Onken, et al., editors, "Integrating Behavioral Therapies with Medications in the Treatment of Drug Dependence," NIDA Research Monograph 150, pp. 1-190 (1995).

Pandey, et al., "Regioselective Generation of Iminium Cation by PET Processes: Its in situ Trapping by Intramolecular Nucleophiles and Synthesis of Some Biologically Active Heterocycles," Tetrahedron, vol. 48(38), pp. 8295-8308, (1992).

Paudel, et al., "Transdermal Delivery of Naltrexone and its Active Metabolite 6-β-Naltrexol in Human Skin in Vitro and Guinea Pigs in Vivo,"Journal of Pharmaceutical Sciences, vol. 94(9), pp. 1965-1975 (2005).

Peh, et al., "Simple liquid chromatographic method for the determination of naltrexone in human plasma using amperometric detection," Journal of Chromatography B, vol. 701, pp. 140-145 (1997).

Porter,et al., "Kinetics and inhibition of the formation of 6β-naltrexol from naltrexone in human liver cytosol," Br. J. Cin Pharmacol, vol. 50, pp. 465-471 (2000).

Reifenrath, et al., "Percutaneous penetration in the hairless dog, weanling pig and grafted athymic nude mouse: evaluation of models for predicting skin penetration in man," British Journal of Dermatology, vol. 111(27), pp. 123-135 (1984).

Reuning, et al., "Testing of Drug Delivery Systems for use in the Treatment of Narcotic Addiction", Nat'l. Inst Drug Abuse Res Monogr. Ser 4, pp. 43-45 (1975).

Roberts, et al., "Correlation of Aqueous and Lipid Solubilities with Flux for Prodrugs of 5-Fluorouracil, Theophylline, and 6-Mercaptopurine: A Potts-Guy Approach," Journal of Pharmaceutical Sciences, vol. 88(5), pp. 515-522 (May 1999).

Rohsenow, et al., "Predictors of Compliance with Naltrexone Among Alcoholics," Alcohol Clin Exp Res, vol. 24(10), pp. 1542-1549 (2000).

Rowland, "Absorption", Clinical Pharmacokinetics, Chapter 9, pp. 119-136, Williams & Wilkins, Media, PA (1995).

Rukstalis, et al., "6-β-Naltrexol Reduces Alcohol Consumption in Rats," Alcohol Clin Exp Res, vol. 24(10), pp. 1593-1596 (2000).

Strasinger, et al., "Prodrugs and codrugs as strategies for improving percutaneous absorption," Expert Reviews Dermatol, vol. 3(2), pp. 221-233 (2008).

Stromberg, et al., "A comparison of the effects of 6-β-naltrexol and naltrexone on the consumption of ethanol or sucrose using a limited-access procedure in rats," Pharmacology, Biochemistry and Behavior, vol. 72, pp. 483-490 (2002).

Sugibayashi, et al.,"Analysis of Simultaneous Transport and Metabolism of Ethyl Nicotinate in Hairless Rat Skin," Pharmaceutical Research, vol. 13(6), pp. 855-860, (1996).

Tojo, et al., "Membrane-Moderated Controlled Release," Mathematical Biosciences, vol. 57, pp. 279-300 (1981).

Valiveti, et al., "Development and validation of a liquid chromatography—mass spectrometry method for the quantitation of naltrexone and 6β-naltrexol in guinea pig plasma," Journal of Chromatography B, vol. 810, pp. 259-267 (2004).

Vandelli, et al., "Gelatin microspheres crosslinked with D,L-glyceraldehyde as a potential drug delivery system: preparation, characterisation, in vitro and in vivo studies," International Journal of Pharmaceutics, vol. 215, pp. 175-184 (2001).

Vereby, Karl, "The Clinical Pharmacology of Naltrexone: Pharmacology and Pharmacodynamics," Naltrexone: Research Monograph 28, Willett, R.E. and Barnett, G., editors, pp. 147-158, (1980).

Volpicelli, et al., "Naltrexone in the Treatment of Alcohol Dependence," Arch Gen Psychiatry, vol. 49, pp. 876-880 (1992).

Volpicelli, et al., "Naltrexone and Alcohol Dependence," Arch Gen Psychiatry, vol. 54, pp. 737-742 (1997).

Wall, et al., "The Metabolism of Naltrexone in Man", Naltrexone: Research Monograph 28, Willett, R.E. and Barnett, G., editors, pp. 105-131, (1980).

Wall, et al., "Metabolism and Disposition of Naltrexone in Man after Oral and Intravenous Administration," Drug Metabolism and Disposition, vol. 9(4), pp. 369-375 (1981).

Wilhelm, et al., "Effect of Sodium Lauryl Sulfate—Induced Skin Irritation on in Vivo Percutaneous Penetration of Four Drugs," Journal of Investigative Dermatology, vol. 97(5), pp. 927-932, (1991).

Wold, "Letters to the Editor—Naltrexone for Alcohol Abuse", J. Am. Acad. Child Adolesc. Psychiatry, vol. 36(1), pp. 6-7. (1997).

Yalkowsky, et al., "Importance of chain length on physiochemical and crystalline properties of organic homologs," Journal of Pharmaceutical Sciences, vol. 61(6), pp. 852-857, (1972).

Yu, et al., "Physical model evaluation of topical prodrug delivery—simultaneous transport and bioconversion of vidarabine-5'-valerate I: physical model development," Journal of Pharmaceutical Sciences, vol. 68(11), pp. 1341-1357, (1979).

Article 19(1) Amendment for PCT/US2007/079336, Apr. 28, 2008.
Informal Comments to Feb. 29, 2008 Written Opinion for PCT/US2007/079336, Dec. 18, 2008.

* cited by examiner

Permeation profile (24 h) of buprenorphine (n=3) in propylene glycol formulation Permeation profile (48 h) of buprenorphine (n=3) in propylene glycol formulation Permeation profile of buprenorphine (n=3), ALL00106 (n=4), and ALL00107 (n=3) in propylene glycol formulation Skin disposition of buprenorphine (n=3), ALL00106 (n=4), and ALL00107 (n=3) in propylene glycol formulation Permeation profile of buprenorphine (n=2), ALL00107 (n=3), and ALL00108 (n=2) in propylene glycol formulation (25% aq. ethanol receiver fluid)

Skin disposition of buprenorphine (n=2), ALL00107 (n=3), and ALL00108 (n=2) in propylene glycol (25% aq. ethanol receiver fluid)

Representative permeation profile of buprenorphine (n=2), ALL00106 (n=3), ALL00107 (n=3), and ALL00108 (n=3) in gel formulation Representative permeation profile of buprenorphine (n=3), ALL00106 (n=3), and ALL00110 (n=2) in propylene glycol Representative permeation profile of buprenorphine (n=3), ALL00108 (n=2), ALL00114 (n=2), and ALL00115 (n=2) in propylene glycol Representative permeation profile of buprenorphine (n=3), ALL00110 (n=3), ALL00114 (n=3), and ALL00115 (n=2) in gel formulation Representative permeation profile of buprenorphine (n=3) and ALL00116 (n=3) in propylene glycol/ethanol [96/4]

Representative permeation profile of buprenorphine (n=2), ALL00113 (n=3), and ALL00116 (n=3) in gel formulation

TRANSDERMALLY DELIVERABLE OPIOID PRODRUGS, ABUSE-RESISTANT COMPOSITIONS AND METHODS OF USING OPIOID PRODRUGS

CROSS-REFERENCE TO RELATED APPLICATIONS

This application is a continuation application of U.S. application Ser. No. 11/860,432, filed on Sep. 24, 2007, which further claims the benefit of U.S. Provisional Application Ser. No. 60/826,603 filed Sep. 22, 2006. These applications, in their entirety, are hereby incorporated by reference.

FIELD

Described herein are pharmaceutically active agents suitable for transdermal delivery to a mammal, compositions for transdermal delivery of pharmaceutically active agents and methods of using such compositions in treating and preventing diseases and disorders.

BACKGROUND

Pain is the most frequently reported symptom and is a common clinical problem which confronts the clinician. Millions of people in the United States suffer from severe pain that, according to numerous recent reports, is chronically under-treated or inappropriately managed.

Opioids have long been recognized as one of the most effective treatments of pain. However, they also have a high potential of abuse. In fact, opioid and narcotic abuse are major worldwide problems connected with tremendous social and personal strife. As of 1992, the estimated United States economic cost of drug and alcohol abuse was $246 billion. The latest National Household Survey on Drug Abuse survey conducted by the Substance Abuse and Mental Health Services Administration reported in July 2007 that nearly one in twelve full-time workers in the United States have serious enough drug/alcohol problems to require medical treatment. Providing recovery assistance for drug addicts and alcoholics with pharmacological interventions has proven helpful.

Certain opioids, such as buprenorphine, butorphanol, dezocine, meptazinol, nalbuphine, and pentazocine, have both agonist and antagonist qualities. For example, the main agonist/antagonist effect of buprenorphine is through its binding to μ-opioid and κ-opioid receptors, acting clinically as an agonist at lower doses and as an antagonist at higher doses. The dual agonist-antagonist activity of these opioids make them effective at not only treating pain, but also at reducing the severity of the withdrawal symptoms experienced when a former abuser begins to eliminate opioid and/or alcohol. Buprenorphine is currently available as a sublingual dosage form, both alone (Subutex®) and in combination with naloxone (Suboxone®) for the treatment of pain and opioid dependence. Because they are administered sublingually, both have clinically relevant drawbacks. For example, the necessity of taking multiple daily doses, or even once-daily dosing, decreases patient compliance. In addition, the daily and multiple daily dosing necessary with sublingual dosage forms may cause more frequent and more extreme peaks and troughs in the blood-plasma concentration of the active medications, thereby, increasing the potential for a patient to experience both the adverse effects associated with supra-therapeutic concentrations and ineffective relief associated with a sub-therapeutic concentrations.

Further, lack of appetite, nausea and/or frequent emesis are commonly experienced by patients undergoing withdrawal from narcotic or alcohol abuse and those suffering from chronic, under-treated or intractable pain. As such, oral and sublingual therapies for these patients are often either poorly tolerated or fail to provide an effective therapeutic dose.

For these patients, transdermal administration can provide a favorable route of administration. Transdermal dosing, provides the patient with a desirable systemic delivery profile which can minimize or eliminate any "highs" (dizziness and drowsiness) associated with more rapid absorption and can reduce the side effects associated with oral administration of a drug such as abdominal pain, nausea and vomiting. Additionally, transdermal administration avoids first-pass metabolism which can allow for higher therapeutic concentrations to be achieved. Transdermal delivery also offers a patient freedom from injections and surgical implantations. Transdermal delivery can also improve patient compliance by reducing the dose frequency. A transdermal patch can offer sustained release of a drug for an extended period (e.g., one week) while transdermal gels are also an accepted dosage form for convenient daily application.

Because of the inherent potential for abuse, it is important that any pharmaceutical composition containing an opioid agonist be made as abuse-resistant or abuse-deterrent as possible. This is particularly true with extended release opioid products, including transdermal applications. Illicit users often will attempt to circumvent the extended release properties of these dosage forms by injecting or otherwise misusing the product in order to achieve an immediate release of the opioid agonist.

Not all opioids however are capable of dermal absorption. Buprenorphine, for example, has been evaluated for transdermal delivery, but has generally been found to be too hydrophobic to cross the skin at a therapeutic rate through a reasonably-sized transdermal patch. However, as transdermal pharmaceutical compositions pass through the epidermis and dermis of many mammals, such as humans and guinea pigs, they are exposed to enzymes which are capable of metabolizing active pharmaceutical agents. The metabolic processes occurring in the skin of mammals, such as humans, can be utilized to deliver pharmaceutically effective quantities of opioids to a mammal in need thereof, by metabolizing prodrugs into active pharmaceutical compounds. Thus, it would be desirable to deliver prodrugs of buprenorphine through the skin at a higher rate than buprenorphine while taking advantage of the rapid hydrolysis of the buprenorphine prodrug to buprenorphine during transport into and through the skin. It would be further desirable to combine the buprenorphine prodrug with a non-dermally absorbable prodrug of an opioid antagonist, such as naltrexone, in order to increase the abuse deterrence of the composition.

SUMMARY

Some embodiments described herein are prodrugs of opioids, including buprenorphine, methods of making prodrugs of buprenorphine, compositions comprising prodrugs of buprenorphine and methods of using prodrugs of buprenorphine.

Other embodiments, objects, features and advantages will be set forth in the detailed description of the embodiments that follow, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DESCRIPTION

Figure 1:
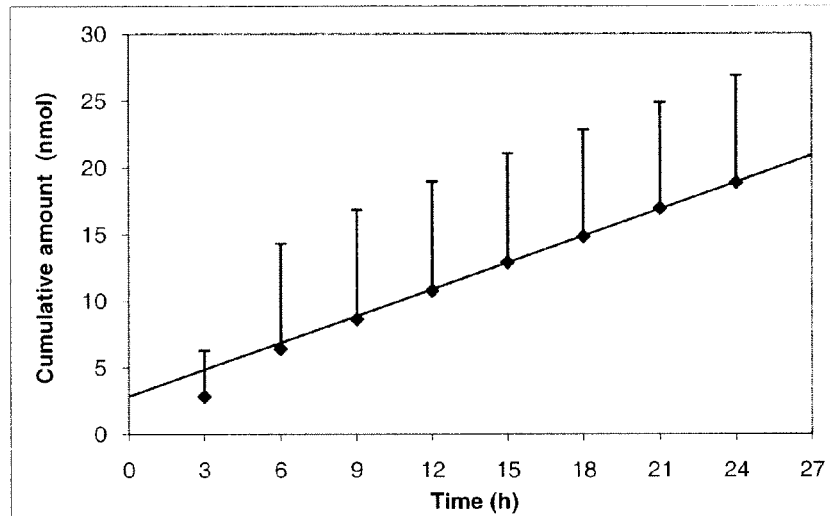
FIG. 1 shows the twenty-four hour permeation profile of buprenorphine (n=3) in a propylene glycol formulation.
Figure 2:
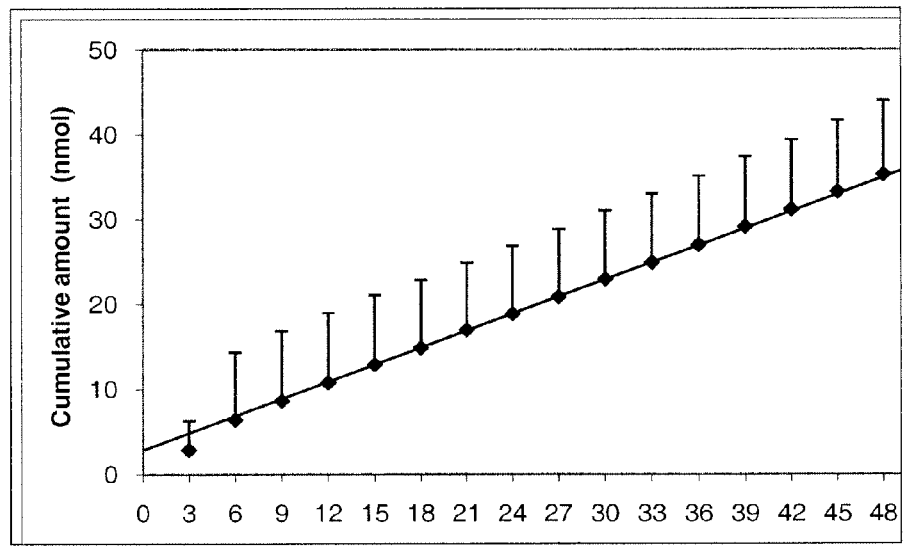
FIG. 2 shows the forty-eight hour permeation profile of buprenorphine (n=3) in a propylene glycol formulation.
Figure 3:
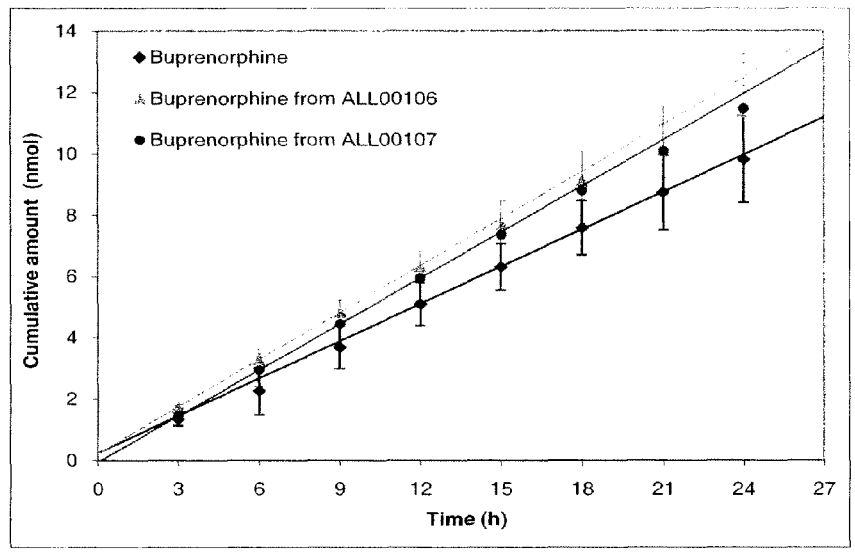
FIG. 3 shows the permeation profile of buprenorphine (n=3), ALL00106 (n=4) and ALL00107 (n=3) in a propylene glycol formulation.
Figure 4:
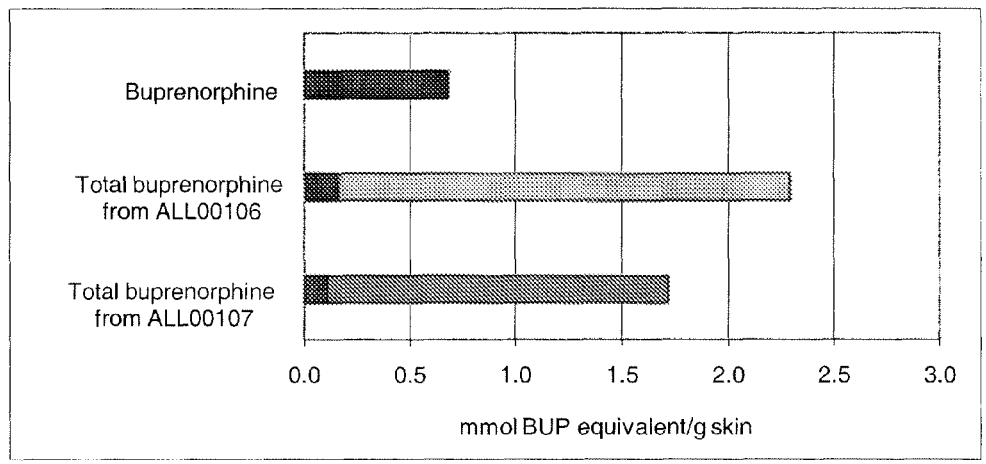
FIG. 4 is a bar graph illustrating the skin disposition of buprenorphine (n=3), ALL00106 (n=4) and ALL00107 (n=3) in a propylene glycol formulation.
Figure 5:
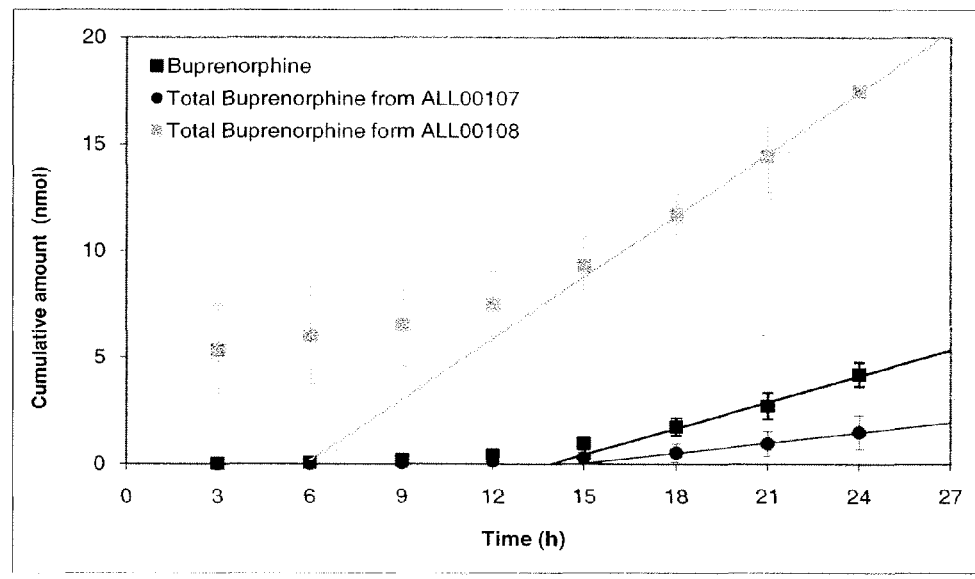
FIG. 5 shows the permeation profile of buprenorphine (n=2), ALL00107 (n=3) and ALL00108 (n=2) in a propylene glycol formulation.
Figure 6:
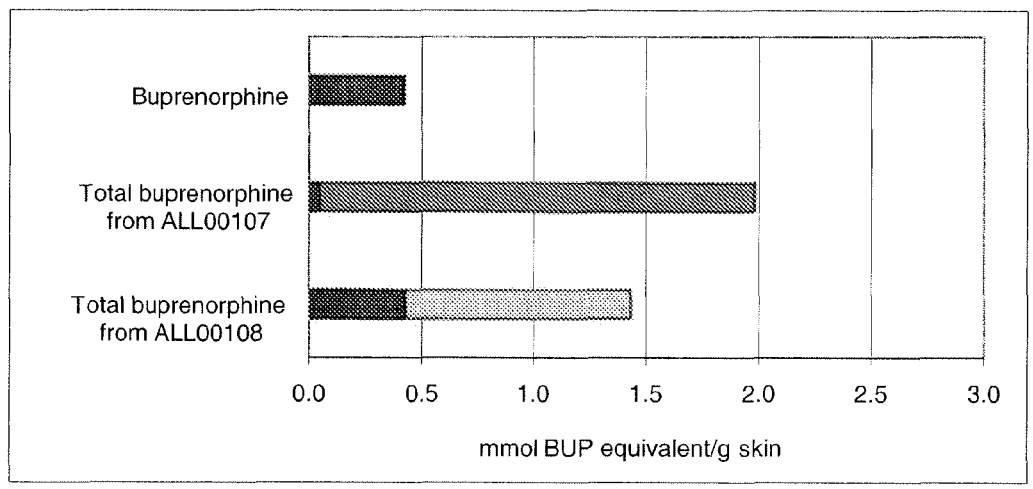
FIG. 6 is a bar graph illustrating the skin disposition of buprenorphine (n=2), ALL00107 (n=3) and ALL00108 (n=2) in a propylene glycol formulation.
Figure 7:
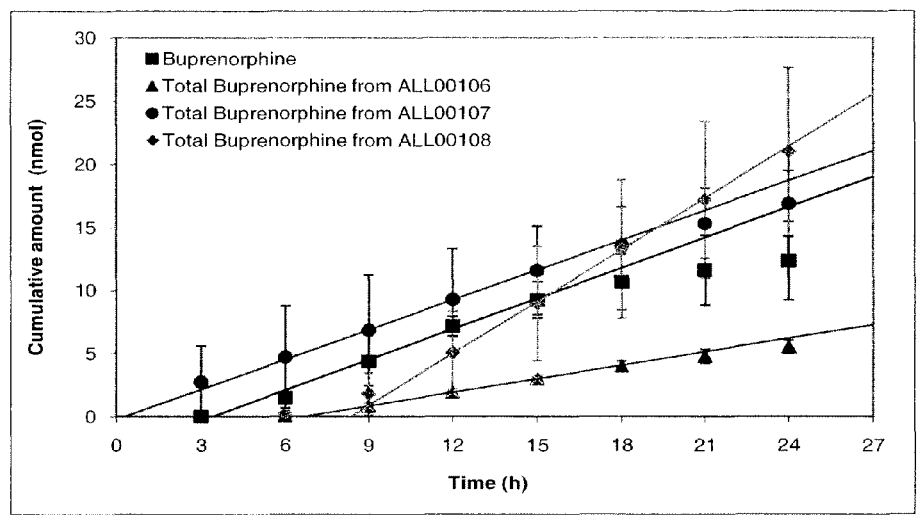
FIG. 7 shows the permeation profile of buprenorphine (n=2), ALL00106 (n=3), ALL00107 (n=3), and ALL00108 (n=3) in a gel formulation.
Figure 8:
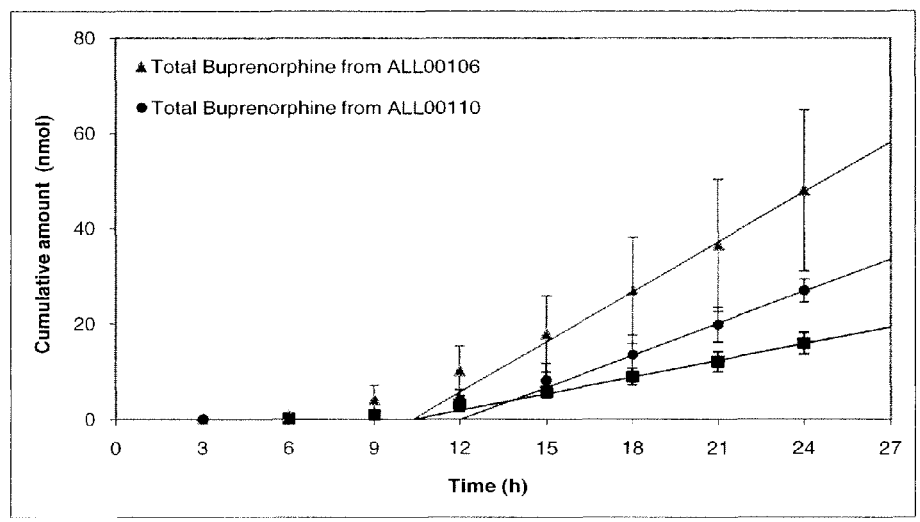
FIG. 8 shows the permeation profile of buprenorphine (n=3), ALL00106 (n=3), and ALL0010 (n=2) in a propylene glycol formulation.
Figure 9:
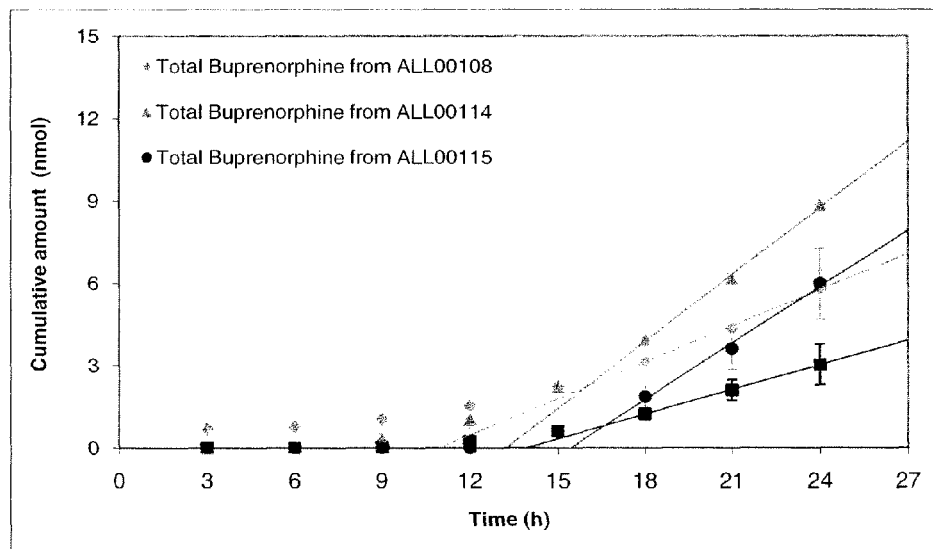
FIG. 9 shows the permeation profile of buprenorphine (n=3), ALL00108 (n=2), ALL0014 (n=2), and ALL0015 (n=2) in a propylene glycol formulation.
Figure 10:
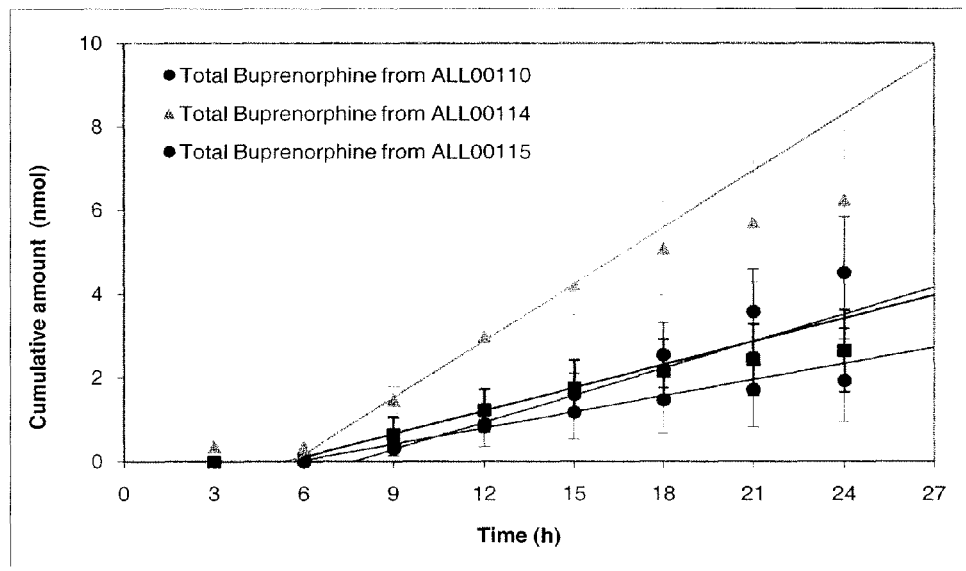
FIG. 10 shows the permeation profile of buprenorphine (n=3), ALL00110 (n=3), ALL00114 (n=3), and ALL00115 (n=2) in a gel formulation.
Figure 11:
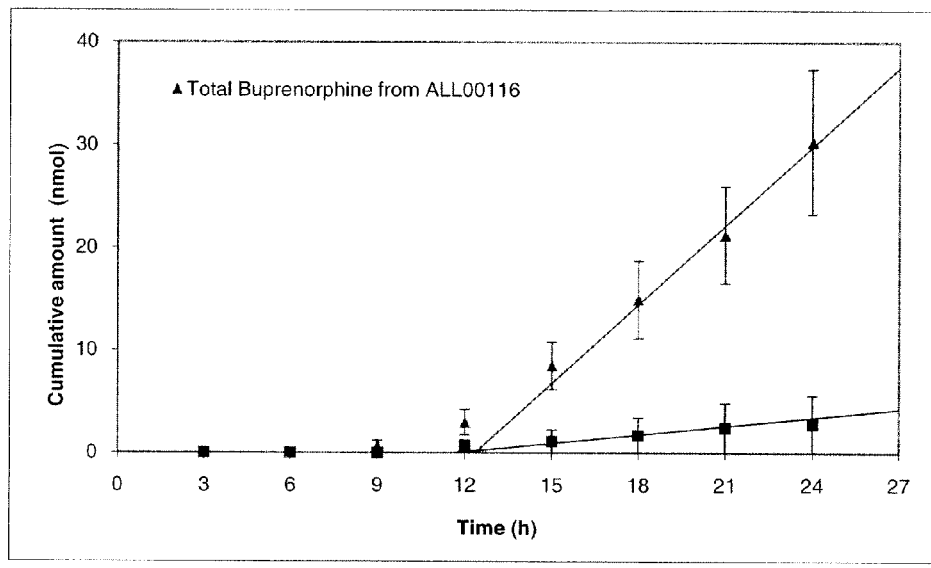
FIG. 11 shows the permeation profile of buprenorphine (n=3) and ALL00116 (n=3) in propylene glycol/ethanol [96/4] formulation.
Figure 12:
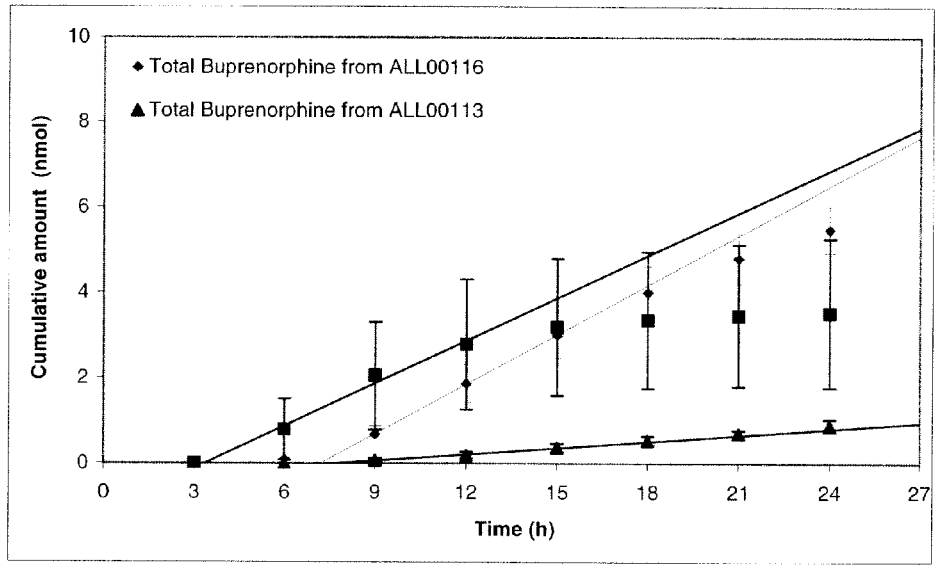
FIG. 12 shows the permeation profile of buprenorphine (n=2), ALL00113 (n=3), and ALL00116 (n=3) in a gel formulation.

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

The term prodrug as used herein refers to a pharmacologically inert chemical derivative that can be converted, enzymatically or non-enzymatically, in vivo or in vitro, to an active drug molecule, which is capable of exerting one or more physiological effects.

Compounds described herein include pharmaceutically acceptable prodrugs of buprenorphine. One embodiment described herein includes pharmaceutically acceptable prodrugs of buprenorphine which are suitable for transdermal administration. The buprenorphine prodrugs described herein may be in any form suitable for administration to a mammal, such as in the form of a free base, free acid, salt, ester, hydrate, anhydrate, enantiomer, isomer, tautomer, polymorph, derivative, or the like, provided that the free base, salt, ester, hydrate, enantiomer, isomer, tautomer, or any other pharmacologically suitable derivative is able to undergo conversion to a therapeutically active form of buprenorphine.

Compositions described herein comprise at least one pharmaceutically acceptable prodrug of buprenorphine. The pharmaceutically acceptable prodrugs of buprenorphine may be in any suitable form for administration to a mammal such as in the form of a free base, free acid, salt, ester, hydrate, anhydrate, amide, enantiomer, isomer, tautomer, polymorph, derivative, or the like, provided that the free base, salt, ester, hydrate, amide, enantiomer, isomer, tautomer, or any other pharmacologically suitable derivative is able to undergo conversion to a therapeutically active form of buprenorphine.

Compositions described herein also include those which are suitable for transdermal administration of prodrugs of buprenorphine and optionally include a vehicle or carrier for the transdermal administration of a prodrug of buprenorphine as well as further comprising one or more of the following: pharmacologically active agents, solvents, thickening agents, penetration enhancers, wetting agents, lubricants, emollients, substances added to mask or counteract a disagreeable odor, fragrances, and substances added to improve appearance or texture of the composition as well as other excipients.

Methods of treating one or more medical conditions such as opioid dependence, alcohol dependence or pain are described herein and comprise administering a pharmaceutically acceptable prodrug of buprenorphine. One embodiment described herein includes pharmaceutically acceptable prodrugs of buprenorphine which are suitable for transdermal administration. The buprenorphine prodrugs described herein may be in any form suitable for administration to a mammal, such as in the form of a free base, free acid, salt, ester, hydrate, anhydrate, enantiomer, isomer, tautomer, polymorph, derivative, or the like, provided that the free base, salt, ester, hydrate, enantiomer, isomer, tautomer, or any other pharmacologically suitable derivative is able to undergo conversion to a therapeutically active form of buprenorphine.

"Pharmaceutically acceptable salts," or "salts," include the salts of buprenorphine prodrugs, suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, beta-hydroxybutyric, galactaric and galacturonic acids. The following list of pharmaceutically acceptable salts is not meant to be exhaustive but merely illustrative as person of ordinary skill in the art would appreciate that other pharmaceutically acceptable salts of buprenorphine and buprenorphine prodrugs may be prepared.

In one embodiment, acid addition salts can be prepared from the free base forms through a reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as person of ordinary skill in the art would appreciate that other acids may be used to create pharmaceutically acceptable salts of buprenorphine and prodrugs of buprenorphine. In other embodiments, an acid addition salt is reconverted to the free base by treatment with a suitable base. In still other embodiments, the basic salts are alkali metal salts, e.g., sodium salt.

In one embodiment, an alkyl carbonate or an oxygenated alkyl carbonate is prepared by functionalizing the 3-phenolic hydroxyl group present within the molecular structure of buprenorphine. In another embodiment, the oxygenated alkyl carbonate is a hydroxylated alkyl carbonate. In a further embodiment the oxygenated alkyl carbonate is an oxa-carbonate. In another embodiment the oxa-carbonate is a pegylated carbonate. In an additional embodiment the alkyl carbonate is methyl carbonate. In further embodiments, the oxygenated alkyl carbonate can have 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, or 14 alkyl carbons. In a further embodiments, the alkyl carbonate has 2 alkyl carbons, 3 alkyl carbons, 4 alkyl carbons, 5 alkyl carbons, 6 alkyl carbons, 7 alkyl carbons or 8 alkyl carbons. In further embodiments the pegylated carbonate can have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units or 8 ethylene glycol repeat units. In further embodiments, the oxygenated alkyl carbonate has 1 oxygen atom, 2 oxygen atoms, 3 oxygen atoms, 4 oxygen atoms, 5 oxygen atoms, 6 oxygen atoms, 7 oxygen atoms, 8 oxygen atoms, 9 oxygen atoms, 10 oxygen atoms, 11 oxygen atoms or 12 oxygen atoms.

In a further embodiment, oxygenated esters are prepared by functionalizing the 3-phenolic hydroxyl group present within the molecular structure of buprenorphine. In a further embodiment the oxygenated esters are oxa-esters. In a further embodiment the oxa-ester is a pegylated ester. In further embodiments the pegylated oxa-esters can have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units or 8 ethylene glycol repeat units. In a further embodiment, the oxygenated ester is an oxygenated alkyl ester. In a further embodiment the oxygenated alkyl ester can be a hydroxylated alkyl ester. In further embodiments, the oxygenated alkyl ester can have 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, or 14 alkyl carbons. In further embodiments, the oxygenated esters have 1 oxygen atom, 2 oxygen atoms, 3 oxygen atoms, 4 oxygen atoms, 5 oxygen atoms, 6 oxygen atoms, 7 oxygen atoms, 8 oxygen atoms, 9 oxygen atoms, 10 oxygen atoms, 11 oxygen atoms or 12 oxygen atoms.

In one embodiment, illustrative opioid prodrugs include those compounds of Formula (I):

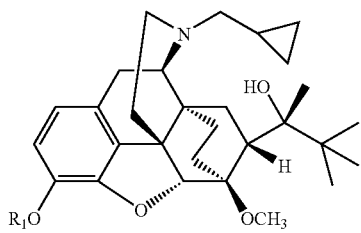

(I)

wherein $R_1$ is comprised of a bio-labile linker (e.g. ester, carbonate, carbamate or other suitable bio-labile linking structure) and further comprising moieties which can be selected in order to control the rate and extent of transdermal absorption and metabolism. Several options for $R_1$ are disclosed herein. Also included herein is the free base, salt, ester, hydrate, amide, enantiomer, isomer, tautomer, polymorph and derivative of compounds of Formula I.

In additional embodiments of compounds of Formula (I), $R_1$ is an alkyl carbonate or an oxygenated alkyl carbonate. In a further embodiment $R_1$ is a hydroxylated alkyl carbonate. In another embodiment $R_1$ is an oxa-carbonate. In a further embodiment $R_1$ is a pegylated carbonate. In an additional embodiment $R_1$ is methyl carbonate. In further embodiments, $R_1$ can be an oxygenated alkyl carbonate and have 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, or 14 alkyl carbons. In a further embodiments, $R_1$ can be an alkyl carbonate and have 2 alkyl carbons, 3 alkyl carbons, 4 alkyl carbons, 5 alkyl carbons, 6 alkyl carbons, 7 alkyl carbons or 8 alkyl carbons. In further embodiments, $R_1$ can be a pegylated carbonate having 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units or 8 ethylene glycol repeat units. In further embodiments, the oxygenated alkyl carbonate has 1 oxygen atom, 2 oxygen atoms, 3 oxygen atoms, 4 oxygen atoms, 5 oxygen atoms, 6 oxygen atoms, 7 oxygen atoms, 8 oxygen atoms, 9 oxygen atoms, 10 oxygen atoms, 11 oxygen atoms or 12 oxygen atoms.

In a further embodiment $R_1$ is an oxygenated ester. In a further embodiment $R_1$ is an oxa-ester. In a further embodiment $R_1$ is a pegylated oxa-ester. In further embodiments, $R_1$ is a pegylated oxa-ester having 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units or 8 ethylene glycol repeat units. In a further embodiment, $R_1$ is an oxygenated alkyl ester. In a further embodiment $R_1$ is a hydroxylated alkyl ester. In further embodiments, $R_1$ is an oxygenated alkyl ester having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, or 14 alkyl carbons. In further embodiments, the oxygenated esters have 1 oxygen atom, 2 oxygen atoms, 3 oxygen atoms, 4 oxygen atoms, 5 oxygen atoms, 6 oxygen atoms, 7 oxygen atoms, 8 oxygen atoms, 9 oxygen atoms, 10 oxygen atoms, 11 oxygen atoms or 12 oxygen atoms.

| Formula | Reference Name | Chemical Name |
|---|---|---|
| II | ALL00106 | Buprenorphine 3,6,9-trioxadecyl carbonate |
| III | ALL00107 | Buprenorphine methyl carbonate |
| IV | ALL00108 | Buprenorphine 2-[2-(2-methoxyethoxy)ethoxy]acetyl ester |
| V | ALL00110 | Buprenorphine 3,4-dihydroxybutyl carbonate |
| VI | ALL00113 | Buprenorphine 3,6-dioxaheptyl carbonate |
| VII | ALL00114 | Buprenorphine 2-(2-methoxyethoxy)acetyl ester |
| VIII | ALL00115 | Buprenorphine 3,6,9,12-tetraoxatridecyl carbonate |
| IX | ALL00116 | Buprenorphine 3,6,9,12-tetraoxatridecanoyl ester |

In a further embodiment, one or more buprenorphine prodrugs are selected from the group consisting of:

Formula (II)
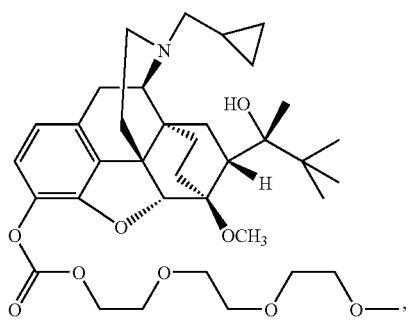
Formula (III)
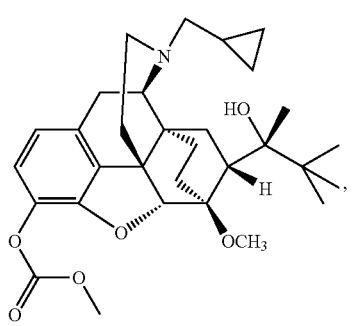
Formula (IV)
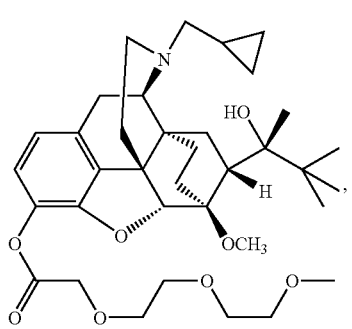
Formula (V)
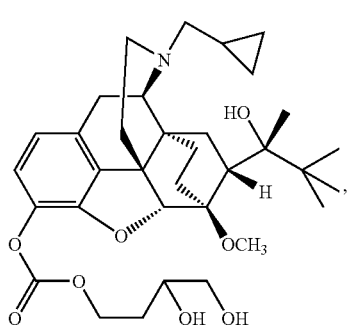
Formula (VI)
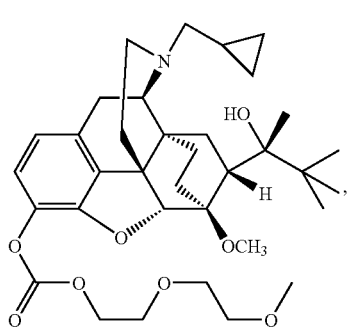
Formula (VII)
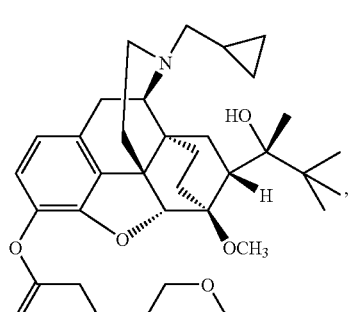
Formula (VIII)
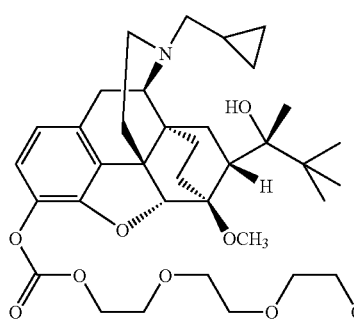
and
Formula (IX)
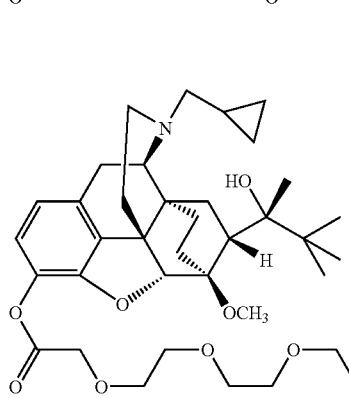
Further embodiments described herein are pharmaceutical compositions comprising (a) a buprenorphine prodrug selected from the group consisting of:
Formula (II)
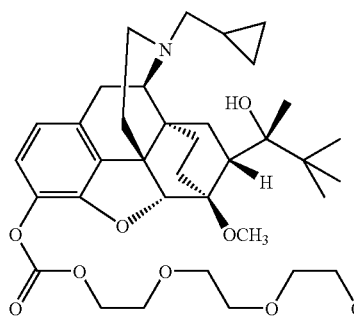

Formula (III)
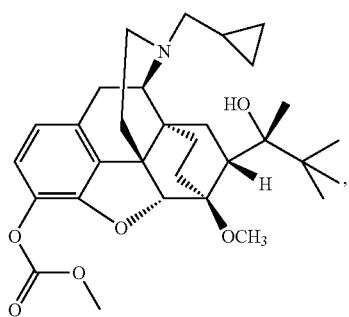
Formula (IV)
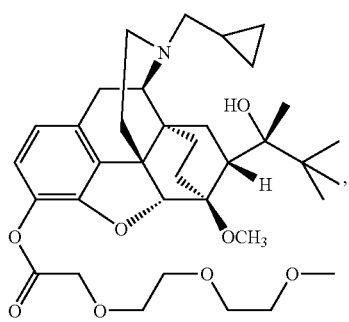
Formula (V)
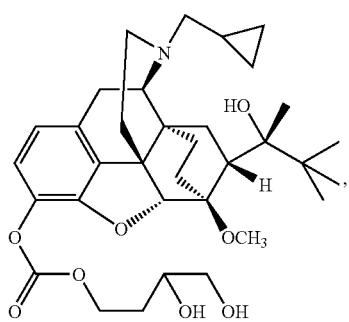
Formula (VI)
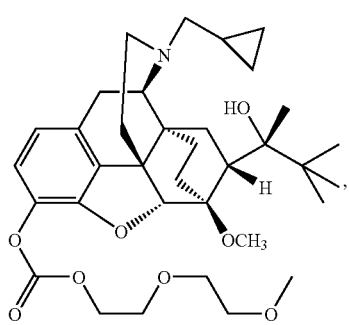
Formula (VII)
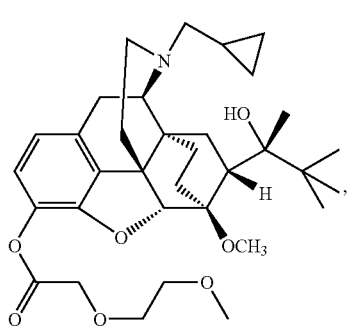
Formula (VIII)
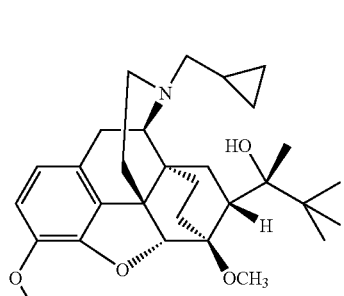
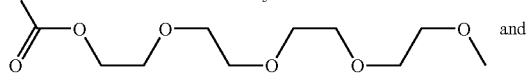
and
Formula (IX)
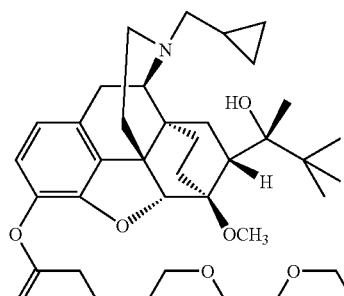
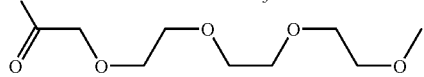
and (b) a pharmaceutical excipient.
Additional embodiments include methods of transdermally delivering a buprenorphine prodrug to a mammal comprising the steps of selecting a buprenorphine prodrug from the group consisting of:
Formula (II)
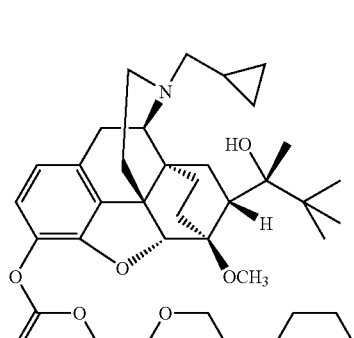
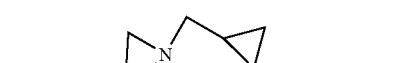
Formula (III)
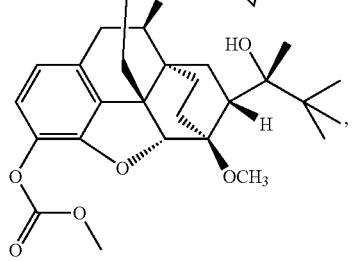

Formula (IV)
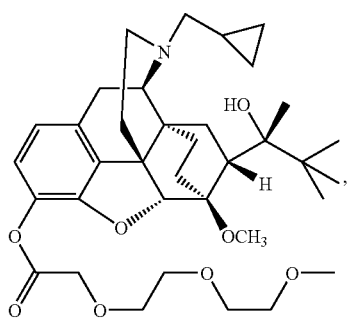

Formula (V)
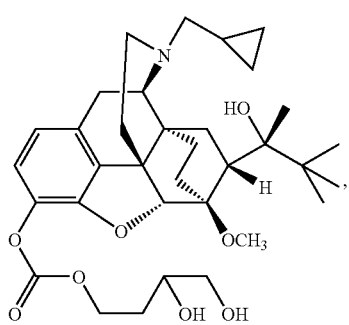

Formula (VI)
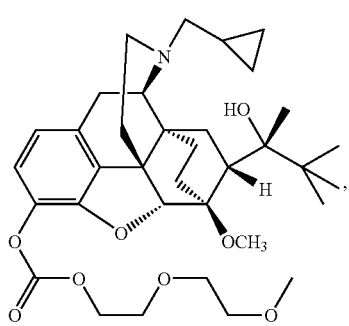

Formula (VII)
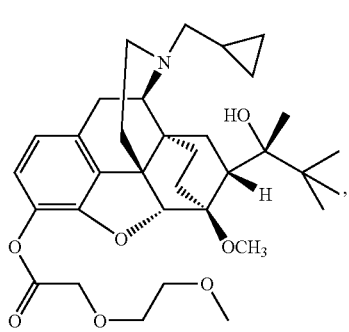

Formula (VIII)
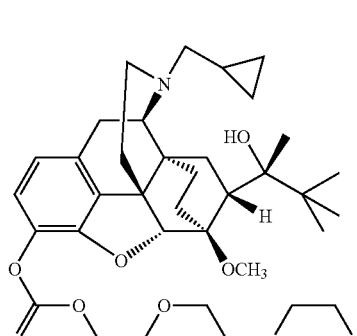 and

Formula (IX)
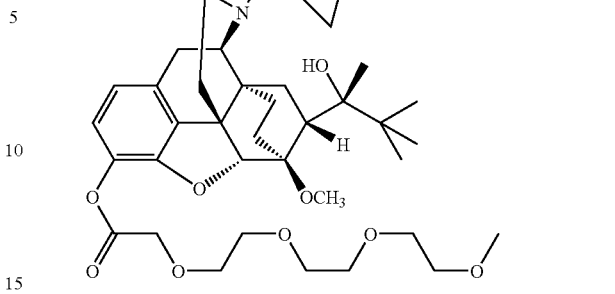

combining the selected compound with a pharmaceutically acceptable excipient to form a pharmaceutical composition and contacting the pharmaceutical composition with the skin of the mammal.

A further embodiment is a method of treating a medical condition in a mammal comprising the steps of administering a buprenorphine prodrug selected from the group consisting of:

Formula (II)

Formula (III)

Formula (IV)
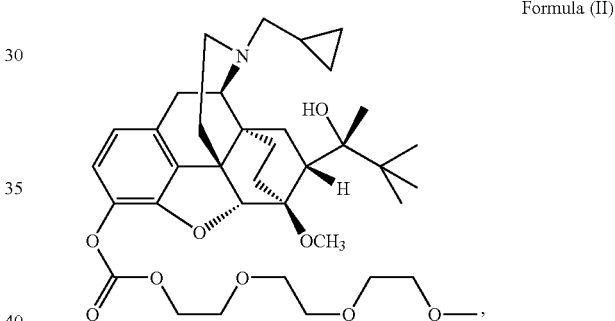

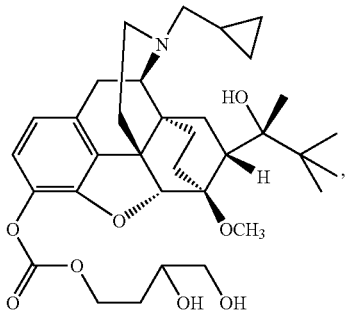
Formula (V)

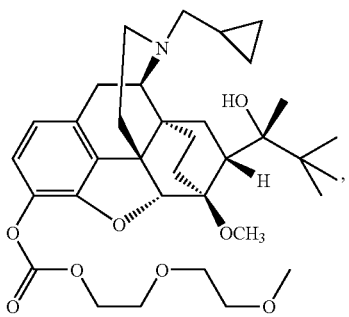
Formula (VI)

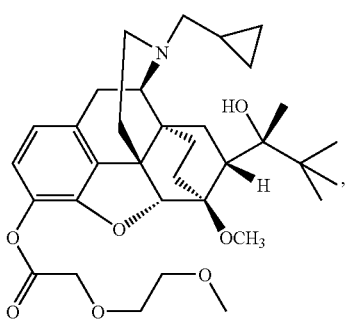
Formula (VII)

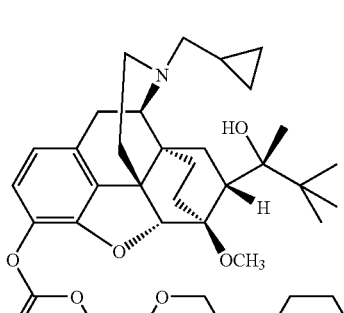
Formula (VIII)

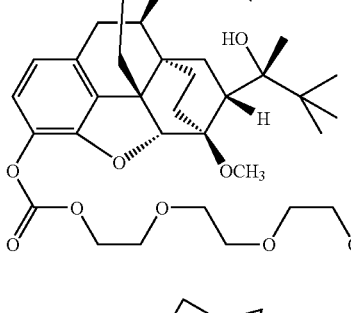
and

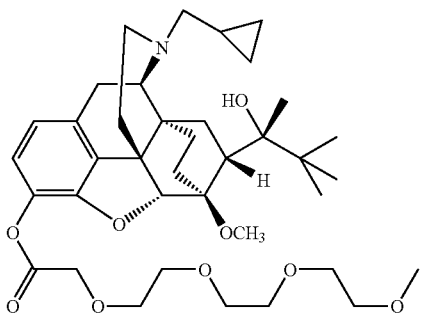
Formula (IX)

In a further embodiment the medical condition is selected from the group consisting of: opioid dependence, alcohol dependence and pain.

Abuse-Resistant Compositions

Due to the potential for opioid agonists and agonist-antagonists drugs to be abused by individuals addicted to opioids, it is desirable to incorporate such compounds into abuse-resistant or abuse-deterrent formulations and dosage forms so that the possibility of abuse through intravenous administration, inhalation, oral ingestion or other methods is substantially reduced or eliminated. For example, with transdermal administration, it is desirable to use poorly absorbed forms of opioid antagonists to minimize the effect of the opioid antagonist during transdermal use, but preserving the antagonist properties in the event that abuse of the dosage form is attempted.

In one embodiment, the pharmaceutical composition contains an opioid agonist or agonist/antagonist such as buprenorphine or prodrugs of an opioid agonist or agonist/antagonist, such as a prodrug of buprenorphine and an opioid antagonist. In a further embodiment, the opioid antagonist is selected from the group consisting of: naltrexone, 6-beta-naltrexol, nalmefene, naloxone and prodrugs of the foregoing.

In a further embodiment, the opioid antagonist would be insoluble in the dosage form and/or not absorbable at a therapeutic rate across the skin.

In a further embodiment, illustrative opioid antagonist prodrugs include those compounds of Formula (X):

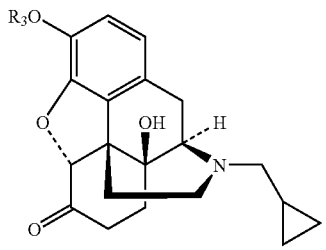

wherein $R_3$ is comprised of a bio-labile linker (e.g. ester, carbonate, carbamate, or other suitable bio-labile linking structure) and further comprising moieties which can be selected in order to control the rate and extent of transdermal absorption and metabolism. Several options for $R_3$ are disclosed herein. Also included herein is the free base, salt, ester, hydrate, amide, enantiomer, isomer, tautomer, polymorph, or derivative thereof of compounds of Formula (X)

In one embodiment, $R_3$ is selected from the group consisting of Formula (X), wherein $R_3$ is selected from the group consisting of:

| | |
|---|---|
| —COC(CH$_3$)$_3$; | Formula (XI) |
| —COCH(CH$_3$)$_2$; | Formula (XII) |
| —COCH$_2$CH(CH$_3$)$_2$; | Formula (XIII) |
| —COCH(CH$_2$CH$_3$)$_2$; | Formula (XIV) |
| —CON(CH$_2$CH$_3$)$_2$; | Formula (XV) |
| CON(CH(CH$_3$)$_2$)$_2$; | Formula (XVI) |
| —COOCH(CH$_3$)$_2$; | Formula (XVII) |

Formula (XVIII):

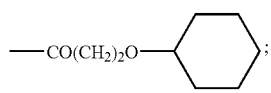

and —CO(CH₂)₂OCH₃. Formula (XIX)

In one embodiment the opioid antagonist is selected from the group consisting of 3-O-pivalyl naltrexone, 3-O-isovaleryl naltrexone, 3-O-(2'-ethylbutyryl) naltrexone, 3-O-isobutyryl naltrexone, 3-O-isopropyloxycarbonyl naltrexone, 3-O-tertiarybutyloxycarbonyl naltrexone, N,N-dimethyl-3-O-carbamate naltrexone, N,N-diethyl-3-O-carbamate naltrexone, and N,N-diisopropyl-3-O-carbamate naltrexone. Other prodrugs of naltrexone, opioid antagonist prodrugs or opioid antagonists can also be used.

Further embodiments are pharmaceutical compositions comprising:

(a) a buprenorphine prodrug selected from the group consisting of:

Formula (II)

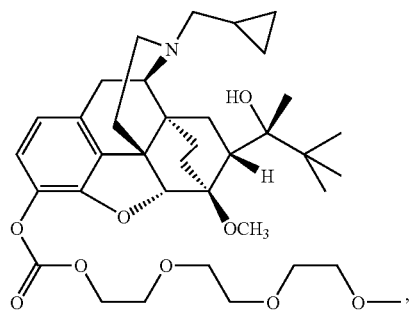

Formula (III)

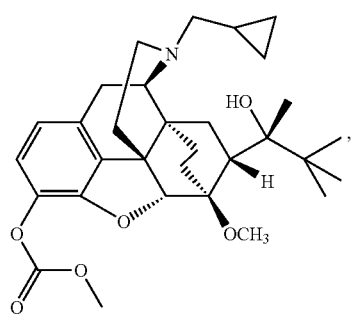

Formula (IV)

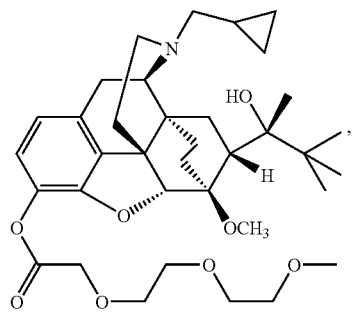

Formula (V)

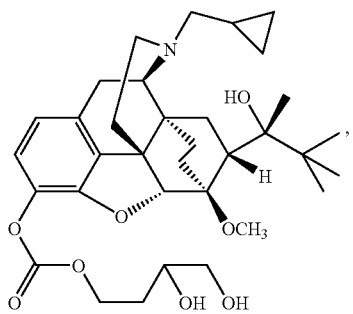

Formula (VI)

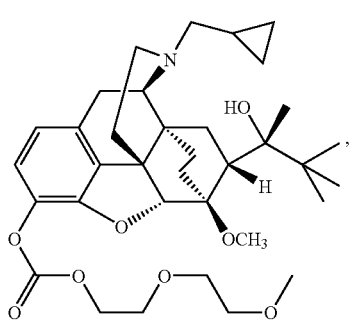

Formula (VII)

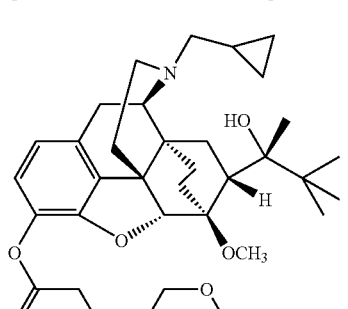

Formula (VIII)

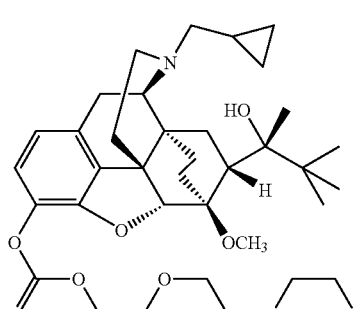

and

Formula (IX)

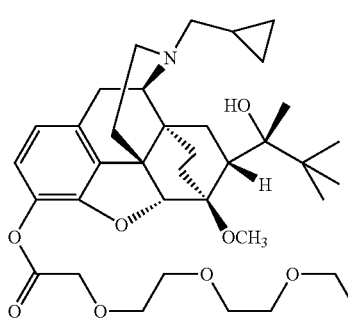

(b) a naltrexone prodrug of Formula (X), wherein $R_3$ is selected from:

—COC(CH₃)₃;      Formula (XI)

—COCH(CH₃)₂;      Formula (XII)

—COCH₂CH(CH₃)₂;      Formula (XIII)

—COCH(CH₂CH₃)₂;      Formula (XIV)

—CON(CH₂CH₃)₂;      Formula (XV)

CON(CH(CH₃)₂)₂;      Formula (XVI)

—COOCH(CH₃)₂;      Formula (XVII)

Formula (XVIII):

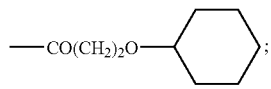

and —CO(CH₂)₂OCH₃; and      Formula (XIX)

(c) a pharmaceutical excipient.

Further embodiments include methods for transdermally delivering a buprenorphine prodrug to a mammal comprising the steps of:

(a) selecting a buprenorphine prodrug from the group consisting of:

Formula (II)

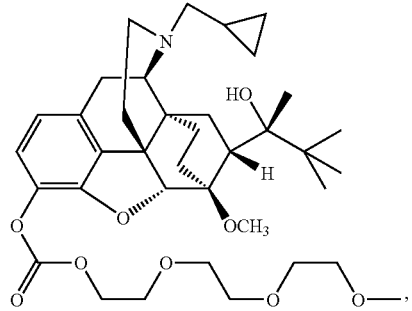

Formula (III)

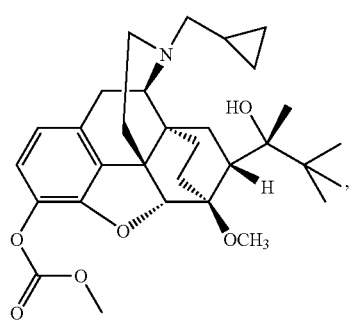

-continued

Formula (IV)

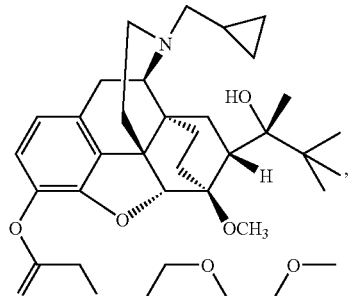

Formula (V)

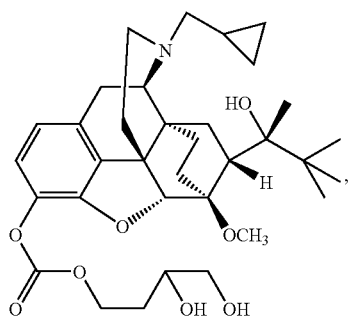

Formula (VI)

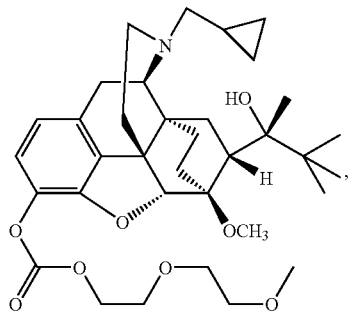

Formula (VII)

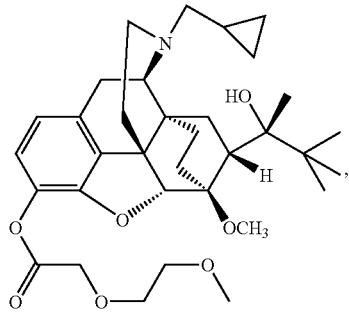

Formula (VIII)

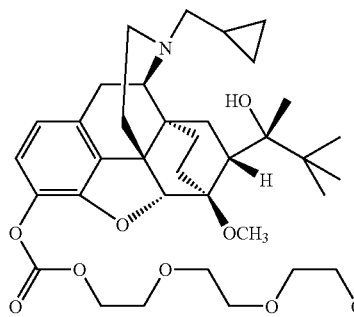

and

Formula (IX)

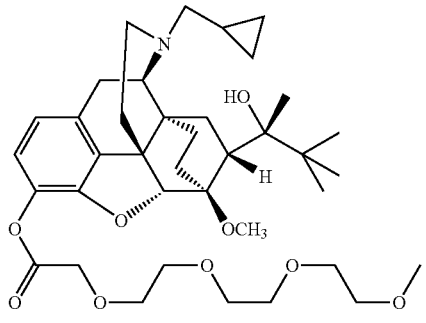

(b) selecting a naltrexone prodrug of Formula (X), wherein $R_3$ is selected from:

—COC(CH₃)₃;                    Formula (XI)

—COCH(CH₃)₂;                   Formula (XII)

—COCH₂CH(CH₃)₂;                Formula (XIII)

—COCH(CH₂CH₃)₂;                Formula (XIV)

—CON(CH₂CH₃)₂;                 Formula (XV)

CON(CH(CH₃)₂)₂;                Formula (XVI)

—COOCH(CH₃)₂;                  Formula (XVII)

Formula (XVIII):

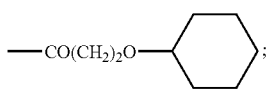

and —CO(CH₂)₂OCH₃;             Formula (XIX)

(c) combining the compounds selected in (a) and (b) with a pharmaceutically acceptable excipient to form a pharmaceutical composition; and
(d) contacting the pharmaceutical composition with the skin of the mammal.

Further embodiments include methods of treating a medical condition in a mammal comprising the step of:
(a) administering a buprenorphine prodrug selected from the group consisting of:

Formula (II)

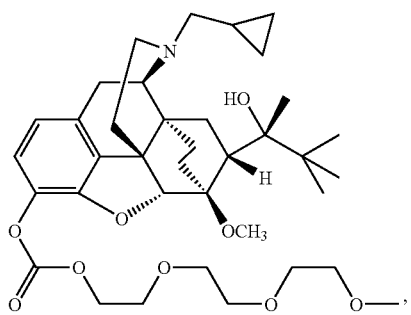

Formula (III)

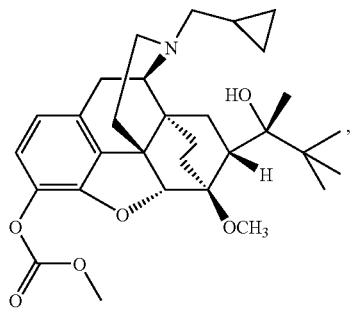

Formula (IV)

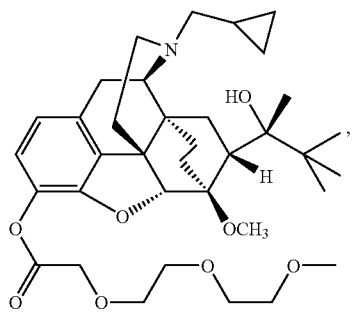

Formula (V)

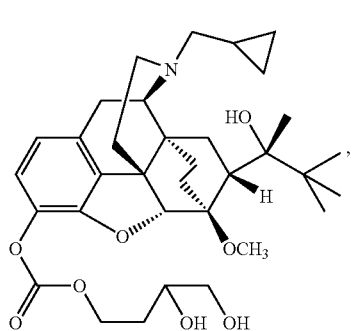

Formula (VI)

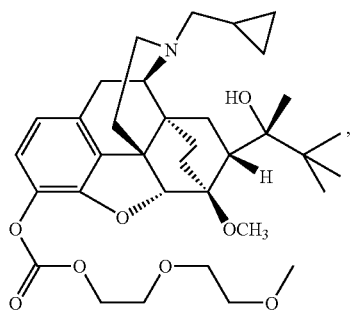

Formula (VII)

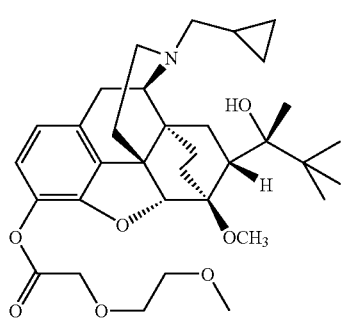

Formula (VIII)

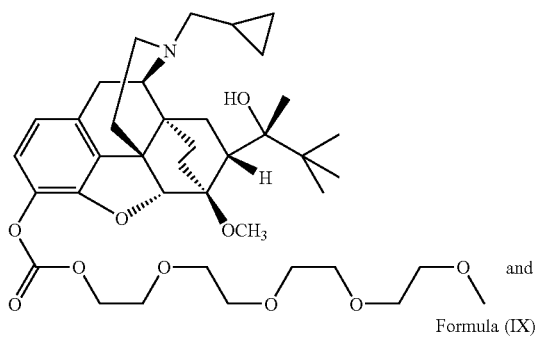

and

Formula (IX)

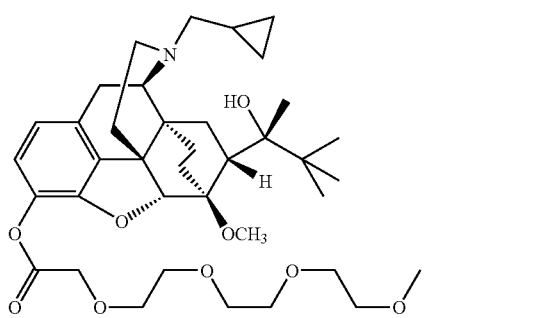

and;

(b) administering a naltrexone prodrug of Formula (X), wherein R₃ is selected from the group consisting of:

—COC(CH₃)₃;                        Formula (XI)

—COCH(CH₃)₂;                       Formula (XII)

—COCH₂CH(CH₃)₂;                    Formula (XIII)

—COCH(CH₂CH₃)₂;                    Formula (XIV)

—CON(CH₂CH₃)₂;                     Formula (XV)

CON(CH(CH₃)₂)₂;                    Formula (XVI)

—COOCH(CH₃)₂;                      Formula (XVII)

Formula (XVIII):

—CO(CH₂)₂O—⟨cyclohexyl⟩;

and —CO(CH₂)₂OCH₃.                 Formula (XIX)

In a further embodiment, the medical condition is selected from the group consisting of: opioid dependence, alcohol dependence and pain.

Combination with Non-Opioid Agents

In one embodiment, the pharmaceutical composition containing the opioid or opioid prodrug could also be combined with an optional second non-opioid pharmacologically active agent for the treatment of pain and/or polydrug abuse, including, for example, a cannabinoid (agonist, antagonist, or inverse agonist), bupropion, hydroxybupropion, nicotine, nomicotine, varenicline, doxepin, acetaminophen, aspirin, or another non-steroidal anti-inflammatory drug. The cannabinoid could consist of one or more of the drugs or prodrugs as described in U.S. patent application Ser. No. 11/157,034 and U.S. Provisional Pat. App. No. 60/952,746. The previous listing of suitable compounds for use as an optional second non-opioid pharmacologically active agent is not meant to be exhaustive, as a person of ordinary skill in the art would understand that other compounds (such as those found in the Merck Index, Thirteenth Edition and the Physicians Desk Reference, 58th ed.) would be suitable for use as the optional second non-opioid pharmacologically active agent in the invention disclosed herein.

Pharmaceutical Excipients

The pharmaceutical compositions described herein can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition. Excipients include, by way of illustration and not limitation, solvents, thickening agents, penetration enhancers, wetting agents, lubricants, emollients, substances added to mask or counteract a disagreeable odor or flavor, fragrances, and substances added to improve appearance or texture of the composition. Any such excipients can be used in any dosage forms of the present disclosure. The foregoing list of excipients is not meant to be exhaustive but merely illustrative as a person of ordinary skill in the art would recognize that additional excipients could be utilized.

Compositions described herein containing excipients can be prepared by any technique known to a person of ordinary skill in the art of pharmacy, pharmaceutics, drug delivery, pharmacokinetics, medicine or other related discipline that comprises admixing one or more excipients with a therapeutic agent.

Non-limiting examples of penetration enhancing agents include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C22 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Additional penetration enhancers suitable for use can also be found in U.S. patent application Ser. No. 10/032,163.

The thickening agents (aka gelling agents) used herein may include anionic polymers such as polyacrylic acid (CARBOPOL® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3, and other polymers such as Pemulen® polymeric emulsifiers, and Noveon® polycarbophils. Additional thickening agents, enhancers and adjuvants may generally be found in Remington's The Science and Practice of Pharmacy as well as the Handbook of Pharmaceutical Excipients, Arthur H. Kibbe ed. 2000. Thickening agents or gelling agents are present in an amount sufficient to provide the desired rheological properties of the composition. Illustratively, one or more pharmaceutically acceptable thickening agent or gelling agent are present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75%, about 10%, about 11%, about 11.5%, about 12%, about 12.5%, about 13%, about 13.5%, about 14%, about 14.5% or about 15%.

In one embodiment a neutralizing agent is optionally present to assist in forming a gel. Suitable neutralizing agents include sodium hydroxide (e.g., as an aqueous mixture), potassium hydroxide (e.g., as an aqueous mixture), ammonium hydroxide (e.g., as an aqueous mixture), triethanolamine, tromethamine (2-amino 2-hydroxymethyl-1,3 propanediol), aminomethyl propanol (AMP), tetrahydroxypropyl ethylene diamine, diisopropanolamine, Ethomeen C-25 (Armac Industrial Division), Di-2 (ethylhexyl) amine (BASF-Wyandotte Corp., Intermediate Chemicals Division), triamylamine, Jeffamine D-1000 (Jefferson Chemical Co.), b-Dimethylaminopropionitrite (American Cyanamid Co.), Armeen CD (Armac Industrial Division), Alamine 7D (Henkel Corporation), dodecylamine and morpholine. The neutralizing agent is present in an amount sufficient to form a gel which is suitable for contact with the skin of a mammal.

In a further embodiment, the formulation is a gel, an ointment, a cream or a patch and comprises a buprenorphine prodrug, optionally one or more penetration enhancing agent, thickening agent, lower alcohol, such as ethanol or isopropanol; or water. In another embodiment, the formulation is a gel, an ointment, a cream or a patch, further comprised of sodium hydroxide or triethanolamine or potassium hydroxide, or a combination thereof, in an amount sufficient, as is known in the art, to assist the gelling agent in forming a gel suitable for contact with the skin of a mammal.

Compositions described herein optionally comprise one or more pharmaceutically acceptable wetting agents as excipients. Non-limiting examples of surfactants that can be used as wetting agents in compositions of the disclosure include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75% or about 10%.

Compositions described herein optionally comprise one or more pharmaceutically acceptable lubricants (including antiadherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. Illustratively, one or more pharmaceutically acceptable lubricants are present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10.0%.

In another embodiment, the compositions described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, althea officinalis extract, arachidyl alcohol, argobase EUC, Butylene glycol dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75 lanolin, sorbitan laurate, walnut oil, wheat germ oil super refined almond, super refined sesame, super refined soybean, octyl palmitate, caprylic/capric triglyceride and glyceryl cocoate.

An emollient, if present, is present in the compositions described herein in an amount of about 1% to about 30%, about 3% to about 25%, or about 5% to about 15%, by weight.

Illustratively, one or more emollients are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%.

In one embodiment, a composition comprises an antimicrobial preservative. Illustrative anti-microbial preservatives include acids, including but not limited to benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. The anti-microbial preservative, if present, is present in an amount of about 0.1% to about 5%, about 0.2% to about 3%, or about 0.3% to about 2%, by weight, for example about 0.2%, 0.4%, 0.6%, 0.8%, 1%, 1.2%, 1.4%, 1.6%, 1.8%, 2%, 2.4%, 2.6%, 2.8%, 3.0%, 3.2%, 3.4%, 3.6%, 3.8%, 4%, 4.2%, 4.4%, 4.6%, 4.8%, or 5%.

Compositions described herein optionally compromise one or more emulsifying agents. The term "emulsifying agent" refers to an agent capable of lowering surface tension between a non-polar and polar phase and includes compounds defined as "self emulsifying" agents. Suitable emulsifying agents can come from any class of pharmaceutically acceptable emulsifying agents including carbohydrates, proteins, high molecular weight alcohols, wetting agents, waxes and finely divided solids. The optional emulsifying agent, if present, is present in a composition in a total amount of about 1% to about 15%, about 1% to about 12%, about 1% to about 10%, or about 1% to about 5% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, or about 15%.

In another embodiment, the water immiscible solvent comprises propylene glycol, and is present in a composition in an amount of about 1% to about 99%, by weight of the composition, for example about 1%, about 2%, about 3%, about 4%, about 5%, about 6%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%.

Pharmaceutical Dosage Forms

In one embodiment, compositions described herein are suitable for transdermal administration. In another embodiment, transdermally administrable compositions are adapted for administration in and/or around the abdomen, back, chest, legs, arms, scalp or other suitable skin surface and maybe formulated as patches, ointments, creams, suspensions, lotions, pastes, gels, sprays, foams, oils or other form suitable for transdermal administration.

In another embodiment, compositions described herein which are transdermally administrable include opioid prodrugs, including prodrugs of buprenorphine, placed in a propylene glycol or gel formulation.

In another embodiment, a single dosage unit comprises a therapeutically effective amount or a therapeutically and/or prophylactically effective amount of buprenorphine or buprenorphine prodrug. The term "therapeutically effective amount" or "therapeutically and/or prophylactically effective amount" as used herein refers to an amount of compound or agent that is sufficient to elicit the required or desired therapeutic and/or prophylactic response, as the particular treatment context may require. Single dosage unit as used herein includes individual sachets containing a single dose, metered pumps designed to dispense a predetermined quantity of material for application to the skin as well as other means for dispensing a single or multiple doses for application to the skin.

It will be understood that a therapeutically and/or prophylactically effective amount of a drug for a subject is dependent inter alia on the body weight of the subject as well as other factors known to a person of ordinary skill in the art. A "subject" herein to which a therapeutic agent or composition thereof can be administered includes mammals such as a human subject of either sex and of any age, and also includes any nonhuman animal, particularly a domestic, farm or companion animal, illustratively a cat, cow, pig, dog or a horse as well as laboratory animals such as guinea pigs and primates.

In another embodiment, compositions disclosed herein comprise one or more opioid prodrugs, including prodrugs of buprenorphine, in a total amount of about of between about 0.1% and about 95% by weight of the composition, for example about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, about 55%, about 60%, about 65%, about 70%, about 75%, about 80%, about 85%, about 90% or about 95%.

A therapeutically effective dose of a opioid prodrug composition described herein is that amount of the composition or opioid prodrug delivered to a mammal for the treatment of a symptom or condition.

The terms "treat", "treated", "treating" and "treatment" are to be broadly understood as referring to any response to, or anticipation of, a medical condition in a mammal, particularly a human, and includes but is not limited to:

(i) preventing the medical condition from occurring in a subject, which may or may not be predisposed to the condition, but has not yet been diagnosed with the condition and, accordingly, the treatment constitutes prophylactic treatment for the medical condition;

(ii) inhibiting the medical condition, i.e., arresting, slowing or delaying the on-set, development or progression of the medical condition; or (iii) relieving the medical condition, i.e., causing regression of the medical condition.

Gel Formulations

Alcoholic gels and emulsions have become more popular for systemic delivery of pharmacologically active agents. Testosterone and estradiol products are examples of products on the market now which are gaining market share relative to competitive patch products. Typically patches have been the mainstay for systemic transdermal drug delivery. Ironically, the original transdermal dosage form was a nitroglycerin ointment that was measured out to provide the correct dose. For modern transdermal systemic delivery, many gels and creams have unit dose packaging and calibrated pump dispensers designed to provide the correct dose for application to the skin of the subject. Systemic gel treatments take advantage of the fact that much larger skin surface areas can be covered with the drug, which will improve the chances of therapeutic blood level success. Patches can usually only be made at a maximum area of 50 cm$^2$; however, this is not a desirable size. Alcoholic gels can be made and can optionally include a gelling agent such as ethyl cellulose or a Carbopol. Optionally, appropriate levels of penetration enhancers can be incorporated into the gel.

Additional embodiments which can be prepared include the following compositions:

| Gel formulation used for rubbing into skin | |
|---|---|
| 92% | absolute ethanol, USP/NF |
| 5% | propylene glycol |
| 2% | Klucel ® hydroxypropylcellulose |
| 1% | buprenorphine or prodrug of buprenorphine Gel formulation |
| 92% | absolute ethanol, USP/NF |
| 5% | ethylene glycol, USP |
| 2% | Klucel ® hydroxypropylcellulose |
| 1% | buprenorphine or prodrug of buprenorphine Gel formulation |
| 91.75% | absolute ethanol, USP/NF |
| 5.0% | ethylene glycol, USP |
| 1% | buprenorphine or prodrug of buprenorphine |
| 1.25% | Di-2 (ethylhexyl) amine |
| 0.5% | Carbopol 980 ®, NF |
| 0.5% | isopropyl myristate, USP/NF |

Patch Formulation

The compounds and pharmaceutical compositions described herein are suitable for use in transdermal delivery devices such as patches and the like. For example, the compounds and compositions described herein are suitable for use in a membrane-modulated transdermal delivery system. In this system, the reservoir containing the compound to be transdermally administered to the patient is encapsulated in a shallow compartment molded from a drug impermeable backing and a rate controlling polymeric membrane through which the compound to be delivered passes in a controlled manner. In one embodiment, the external surface of the membrane has a thin layer of a drug-compatible, hypoallergenic adhesive polymer (e.g., silicone or polyacrylate adhesive) which is applied to achieve intimate contact of the transdermal system with the skin.

The compounds and pharmaceutical compositions described herein are also suitable for use in adhesive-diffusion controlled transdermal systems. In these embodiments, the drug reservoir is formulated by directly dispersing the drug (or drugs) to be delivered in an adhesive polymer and then spreading the medicated adhesive onto a flat sheet of drug-impermeable backing membrane to form a thin drug reservoir layer. Optionally, on top of the drug reservoir layer, additional layers of non-medicated rate controlling adhesive polymer of constant thickness are placed to produce an adhesive diffusion-controlled drug-delivery system.

The compounds and pharmaceutical compositions described herein are also suitable for use in matrix dispersion-type systems. In these systems, the drug reservoir is formed by homogeneously dispersing the drugs in a hydrophilic or lipophilic polymer matrix, and the medicated polymer then is molded into a medicated disc with a defined surface area and controlled thickness. The disc then is glued onto an occlusive baseplate in a compartment fabricated from a drug-impermeable backing. The adhesive polymer is spread along the circumference to form a strip of adhesive rim around the medicated disc.

The compounds and pharmaceutical compositions described herein are also suitable for use in microreservoir systems. In these systems, the drug reservoir is formed by first suspending the drug particles in an aqueous solution of water-soluble polymer and then dispersing it homogeneously in a lipophilic polymer by high-shear mechanical force to form a large number of unleachable, microscopic spheres of drug reservoirs. This unstable dispersion is quickly stabilized by immediately cross-linking the which produces a medicated polymer disc with a constant surface area and fixed thickness. A transdermal therapeutic system is produced in which the medicated disc is positioned at the center and surrounded by an adhesive rim.

Patch formulations can be optimized using in vitro human skin diffusion testing prior to the selection of two or three patches for stability testing. In one embodiment, the drug and adhesive are formulated into one monolithic layer. The drug can be mixed with an adhesive (e.g. silicone type, available from Dow Corning and other manufacturers) in a solvent (e.g. methylene chloride or ethyl acetate). This drug mixture would then be extruded onto a polyester backing film to a uniform thickness of about 100 microns or greater with a precision wet film applicator. The solvent is allowed to evaporate in a drying oven and the resulting "patch" is trimmed to fit the diffusion cell donor chamber. Various patch formulations will be made until the desired steady-state flux rate and adhesive properties are obtained. Different adhesives can be tried, as well as varying the amount of adhesive in the formulation (Nalluri, Milligan et al. 2005). Suitable results have been obtained by making monolithic patches with DURO-TAK 387-2051, which is an acrylate-vinyl acetate non-curing pressure sensitive adhesive from the National Starch Chemical Company. Different solvents (e.g. isopropyl myristate, propylene glycol) can optionally be incorporated into the formulation in an attempt to optimize the delivery rate. In a further embodiment, reservoir patches can be made if it appears, for example, that the drugs are not compatible with a monolithic matrix patch formulation. In the reservoir system, the active ingredient(s) and any excipient(s) could be formulated into a gel and sealed between a release layer and an impermeable backing material such as polyester or other suitable material known to a person of skill in the art. Ethyl vinyl acetate membranes with acrylic adhesives have been found to be suitable.

Adhesive patch formulations can be prepared containing different loadings of a buprenorphine prodrug and optionally an opioid antagonist by using DURO-TAK adhesives (National Starch and Chemical Company, USA). Appropriate amounts of adhesive and drug can be sonicated for ten minutes, cast onto the release liner (9742 Scotchpak, 3M, St. Paul, Minn.) with a wet film applicator (Paul N. Gardner Company, Inc., Pompano Beach, Fla.) set at a 40 mil thickness, and kept at room temperature for one hour and then at 70° C. in an oven for ten minutes (to remove any residual solvent). The patches would then be covered with backing membrane (CoTran 9722, 3M, St. Paul, Minn.), will be cut into appropriate sizes, and then can be stored in a desiccator for further study.

In further embodiments, additional adhesives which are suitable for preparing patch formulations and transdermal delivery devices such as patches include polyisobutylenes, acrylates, silicone and combinations of the foregoing. Additional adhesives can be found in U.S. Provisional Patent Application No. 60/852,394.

In another illustrative embodiment, the transdermal patch can be one which is capable of controlling the release of the buprenorphine or buprenorphine prodrug such that transdermal delivery of the buprenorphine or buprenorphine prodrug to the subject is substantially uniform and sustained over a period of about 6 hours, about 12 hours, about 24 hours, about 48 hours or about 7 days. Such transdermal patch which can be used in the practice of the methods described herein can take the form of an occlusive body. In practice, the occlusive body which includes the buprenorphine or buprenorphine prodrug is positioned on the subject's skin under conditions effective to transdermally deliver the buprenorphine or buprenorphine prodrug to the subject.

In addition to using the compounds and pharmaceutical compositions described herein in the transdermal delivery systems previously described, they are also suitable for use in conjunction with microneedles for transdermal drug delivery which create micrometer-scale transport pathways. Microneedles provide a minimally invasive means to transport molecules into the skin, as the channels they create are extremely small on a clinical level. However, because the channels are much larger than even macromolecules, such channels should dramatically increase skin permeability.

Microneedles can be made from materials such as silicon, biodegradable polymers, and stainless steel as well as other bio-compatible materials and can be solid or hollow. Solid microneedles can be used to create holes in the skin, followed by application of a transdermal patch to the skin surface. Alternatively, solid microneedles can be first coated with a drug and then inserted into the skin. Hollow microneedles can also be used, to facilitate active fluid flow through the needle bore and into the skin. See, e.g., Prausnitz, Adv. Drug. Deliv. Rev. 56 (2004) 581-587, for a review.

Numerous studies have demonstrated that solid microneedles can increase skin permeability by up to four orders of magnitude for compounds ranging in size from small molecules to proteins to nanoparticles (Henry et al., J. Pharm. Sci. 87 (1988) 922-925; McAllister et al., PNAS 100 (2003) 13755-13760; Lin et al., Pharm. Res. 18 (2001) 1787-1793; and Cormier et al., J. Control. Release. 97 (2004) 503-511). Hollow microneedles have also been shown to deliver insulin and reduce blood glucose levels (McAllister et al., PNAS 100 (2003) 13755-13760; Martanto et al., Pharm. Res. 21 (2004) 947-952). Kaushik et al. studied the effects of pain associated with microneedle insertion in human volunteers and showed that the sensation was no more than that of a smooth surface applied to the skin or the "sensation of a piece of tape" applied to the skin (Kaushik et al., Anesth. Analg. 92 (2004) 502-504).

Suitable microneedle arrangements for use with the compounds and compositions described herein can be found in the foregoing references as well as in U.S. patent application Ser. No. 11/812,249.

EXAMPLES

Example 1

Section I

Summary

The objective was to synthesize buprenorphine and buprenorphine prodrugs and assess the permeation of buprenorphine and its prodrugs through human abdominal skin in vitro. Buprenorphine base and eight buprenorphine prodrugs were synthesized and tested. Flow through diffusion cells were used for the permeation studies. An aqueous ethanol solution of 25% was used for the receiver solution. Donor compartment was comprised of 100% propylene glycol solution, 96% propylene glycol with 4% ethanol or a gel formulation. The flux and lag time values of buprenorphine and buprenorphine prodrugs were obtained from the permeation profiles. Drug accumulation in the skin after a 24 h diffusion experiment was determined as μmol/g wet tissue weight.

Section II

Methodology 1.0 Purpose: Synthesize buprenorphine prodrugs and assess the human skin permeation of buprenorphine and buprenorphine prodrugs in vitro. The following compounds were studied:

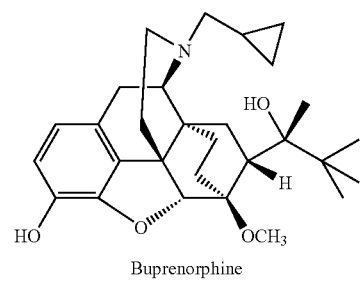

Buprenorphine

Formula (II)

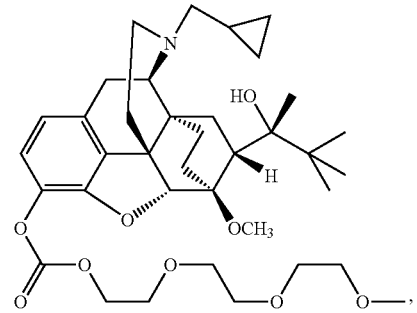

Formula (III)

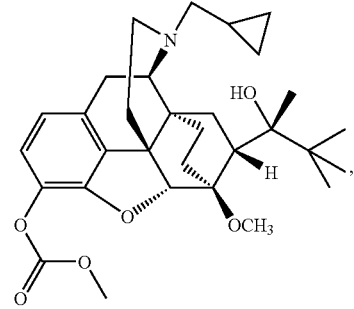

Formula (IV)

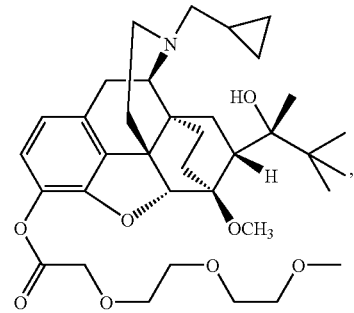

-continued

Formula (V)
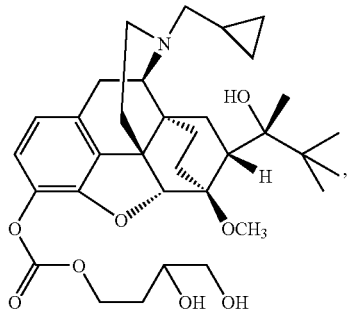

Formula (VI)
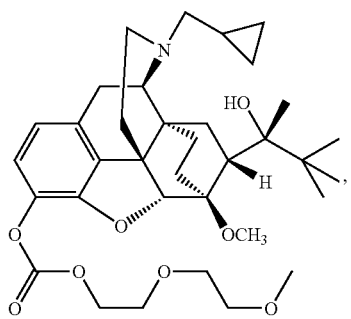

Formula (VII)
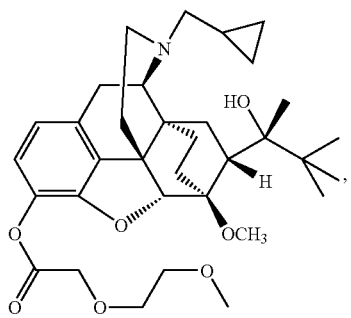

Formula (VIII)
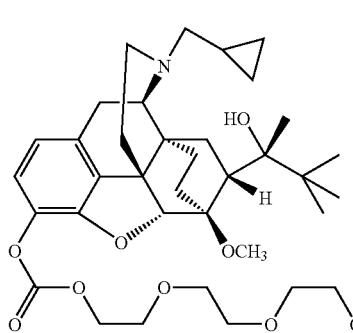

and

Formula (IX)
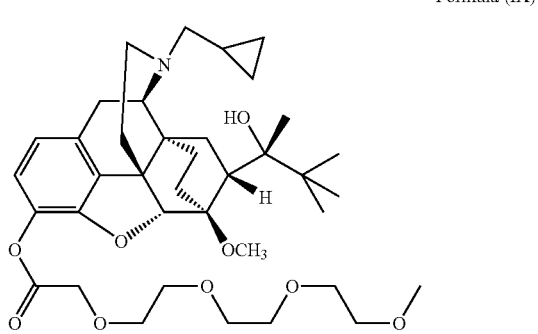

2.0 Skin Details

The skin samples used in the following experiments were obtained from the abdominal reduction surgery and dermatomed to a thickness of approximately 200 µm. The skin samples used herein were frozen at −20° C. for less than one year.

3.0 Chemicals

Acetonitrile (HPLC grade), trifluoroacetic acid, triethylamine, 4-(2-hydroxy ethyl)-piperzine ethane sulfonic acid (HEPES), gentamicin sulfate, acetone, sodium hydroxide, 4-dimethylaminopyridine, and sodium bicarbonate were obtained through Fisher Scientific (Fair Lawn, N.J.). Methanol (HPLC grade), acetonitrile (HPLC grade), N—N'-dicyclohexylcarbodiimide, and polyethylene glycol 400 (PEG 400) were obtained through VWR (West Chester, Pa.). Propylene glycol (PG), triethylene glycol, buprenorphine hydrochloride, triphosgene, methylchloroformate, butenyl chloroformate, osmium tetraoxide, and Hanks' balanced salts modified powder were purchased from Sigma-Aldrich (St. Louis, Mo.). Petroleum ether, ethyl acetate, hexane, chloroform, anhydrous sodium sulfate, hexane, methylene chloride, and dichloromethane were obtained from the Chemical Stores (Lexington, Ky.). Argon and nitrogen were purchased through Scott Gross Company, Inc. (Lexington, Ky.). Nanopure water was obtained from a Barnstead NANOpure® Diamond™ Ultrapure water system (Barnstead International, Dubuque, Iowa).

4.0 Synthesis of Buprenorphine Base and Buprenorphine Prodrugs 4.1 Synthesis of Buprenorphine Base Buprenorphine hydrochloride (200 mg, 0.0004 mol) was suspended in about 10 mL of dichloromethane. Triethylamine (80 mg, 0.0008 mol) was added drop-by-drop. The solution was stirred until all material had dissolved. The solution was transferred to a 60-mL separatory funnel with rinses of dichloromethane. About 10 mL of water was added to the funnel and the contents agitated well by hand. The two phases were allowed to separate. The methylene chloride layer was removed and dried over anhydrous sodium sulfate for several hours. The methylene chloride was removed and combined with dichloromethane rinses of the sodium sulfate. The solvent was removed by a stream and nitrogen and the final product dried under vacuum.

4.2 Synthesis of ALL00106 (Buprenorphine 3,6,9-trioxadecyl Carbonate)

Triethylene glycol monomethyl ether (60 mg, 0.0004 mol) was dissolved in dichloromethane and the solution chilled in an ice bath. Triphosgene (36 mg, 0.00013 mol) was dissolved in dichloromethane and this solution slowly added to the triethylene glycol solution with stirring and while maintained at 0° C. The mixture was kept under argon and stirred for 3 hours.

Buprenorphine hydrochloride (200 mg, 0.0004 mol) was suspended in about 10 mL of dichloromethane. Triethylamine (80 mg, 0.0008 mol) was added drop-by-drop. The solution was sealed and stirred for 3 hours.

The two solutions were combined and allowed to come to ambient temperature. The mixture was placed under argon and allowed to stir overnight. The solvent was reduced to a small volume under nitrogen and hexane was added to precipitate the product. The product was removed by filtration and dried under vacuum. The resulting product was a white, slightly sticky powder.

4.3 Synthesis of ALL00107 (Buprenorphine Methyl Carbonate)

Buprenorphine hydrochloride (204 mg, 0.0004 mol) was suspended in 10 mL of dichloromethane contained in a glass vial. The vial was placed in an ice bath and the contents chilled to 0° C. Triethylamine (121 mg, 0.0012 mol) was added slowly while stirring. Methylchloroformate (75.6 mg, 0.0008 mol) was added drop-wise while stirring. The solution was allowed to come to ambient temperature and left to stir overnight. The solution was reduced to about 1 mL under a stream of nitrogen. About 5 mL of hexane were added to precipitate the product. Solvent was removed under a stream of nitrogen and then by vacuum until constant weight for the product was obtained. The resultant product was a white powder.

For ALL00107, the $^1$H NMR (400 MHz, CDCl$_3$) was as follows: δ=6.86 (1H, d, J=8.0); 6.60 (1H, d, J=8.0); 5.90 (1H, s, H-5); 4.46 (1H, d, J=1.8); 3.85 (3H, s, OCO$_2$CH$_3$); 3.49 (s, 3H); 3.06-2.98 (2H, m); 2.93-2.84 (1H, m); 2.62 (1H, dd, J1=11.9, J2=5.1); 2.38-2.21 (4H, m); 2.12 (1H, t, J=9.9); 1.98 (1H, dt, J1=12.7, J2=5.6); 1.94-1.78 (2H, m); 1.71 (1H, dd, J1=12.9, J2=2.2); 1.35 (3H, s, CH$_3$C), 1.32 (1H, dd, J1=13.2, J2=9.4); 1.12-1.03 (1H, m); 1.03 (9H, s, C(CH$_3$)$_3$); 0.85-0.74 (1H, m); 0.72-0.62 (1H, m); 0.55-0.43 (2H, m, c-Pr); 0.16-0.07 (2H, m, c-Pr).

4.4 Synthesis of ALL00108 (Buprenorphine 2-[2-(2-methoxyethoxy)ethoxy]acetyl Ester)

2-[2-(2-methoxyethoxy)ethoxy]acetic acid (37 mg, 0.0002 mol), N—N'-dicyclohexylcarbodiamide (62 mg, 0.0003 mol) and 4-dimethylaminopyridine (2.4 mg, 0.00002 mol) were combined in dichloromethane and covered with argon. The mixture was allowed to stir at ambient temperature for 3 hours.

Buprenorphine hydrochloride (100 mg, 0.0002 mol) was suspended in dichloromethane. The above mixture was slowly added. The mixture was kept under argon and stirred at ambient temperature overnight.

The solvent was reduced to a small volume under nitrogen and hexane was added to precipitate the product. The product was removed by filtration and dried under vacuum. The resulting product was an off-white powder.

For ALL00108, the $^1$H NMR (400 MHz, CDCl$_3$) was as follows: δ=6.83 (1H, d, J=8.0); 6.62 (1H, d, J=8.0); 5.88 (1H, s, H-5); 4.45 (1H, d); 4.39 (2H, s, OCH$_2$CO$_2$); 3.80-3.76 (2H, m, PEG); 3.73-3.63 (4H, m, PEG); 3.57-3.53 (2H, m, PEG); 3.45 (s, 3H); 3.38 (s, 3H, CH$_2$OCH$_3$); 3.06-2.98 (2H, m); 2.93-2.84 (1H, m); 2.62 (1H, dd, J1=11.9, J2=5.1); 2.38-2.21 (4H, m); 2.12 (1H, t, J=9.9); 1.98 (1H, dt, J1=12.7, J2=5.6); 1.94-1.78 (2H, m); 1.71 (1H, dd, J1=12.9, J2=2.2); 1.35 (3H, s, CH$_3$C), 1.32 (1H, dd, J1=13.2, J2=9.4); 1.12-1.03 (1H, m); 1.04 (9H, s, C(CH$_3$)$_3$); 0.85-0.74 (1H, m); 0.72-0.62 (1H, m); 0.55-0.43 (2H, m, c-Pr); 0.16-0.07 (2H, m, c-Pr).

4.5 Synthesis of ALL0010 (Buprenorphine 3,4-dihydroxybutyl Carbonate)

Buprenorphine hydrochloride (300 mg, 0.0006 mol) was suspended in dichloromethane. Triethylamine (171 mg, 0.0012 mol) was added slowly with stirring. After all material had dissolved, 3-butenyl chloroformate (81 mg, 0.0006 mol) was added slowly under argon with stirring. The mixture was allowed to stir overnight under argon at ambient temperature. The solution volume was reduced to about 2 mL under a stream of nitrogen. Hexane was added to precipitate the product (3-butenyl carbonate of buprenorphine), which was recovered by filtration and dried under vacuum. The recovered 3-butenyl carbonate of buprenorphine (360 mg, 0.0007 mol) was dissolved in 10% water in acetone. Pyridine (53 mg, 0.0007 mol) was slowly added under argon with stirring, followed by N-methylmorpholine N-oxide (189 mg, 0.0014 mol) and the mixture brought to 0° C. in an ice bath. Osmium tetraoxide (48 mg, 0.0007 mol) was dissolved in 10% water in acetone and added slowly under argon at 0° C. with stirring. The mixture was allowed to come to ambient temperature and continue to stir overnight. The solution was transferred to separatory funnel and additional water added. Dichloromethane was added and the two phases mixed thoroughly by manual shaking. After phase separation, the methylene chloride layer was removed and dried for several hours over anhydrous sodium sulfate. The solution volume was reduced under a stream of nitrogen and hexane was added to precipitate the final product. The product was recovered by filtration and dried under vacuum.

4.6 Synthesis of ALL00113 (Buprenorphine 3,6-dioxaheptyl Carbonate)

The same procedure as for ALL00106, starting from diethylene glycol monomethyl ether (36 mg, 0.3 mmol), triphosgene (26.7 mg, 0.09 mmol), Buprenorphine hydrochloride (150 mg, 0.3 mmol) and triethylamine (60.6 mg, 0.6 mmol), afforded 8 mg (4%) of ALL00113.

4.7 Synthesis of ALL0014 (Buprenorphine 2-(2-methoxyethoxy)acetyl Ester)

The same procedure as for ALL00116, starting from Buprenorphine hydrochloride (150 mg, 0.3 mmol), triethylamine (33.3 mg, 0.33 mmol), 2-(2-methoxyethoxy)acetic acid (40.2 mg, 0.3 mmol), 4-dimethylaminopyridine (3.7 mg, 0.03 mmol) and N—N'-dicyclohexylcarbodiimide (92.8 mg, 0.45 mmol), afforded 98 mg (56%) of ALL00114 as an off-white oil.

For ALL00114, the $^1$H NMR (400 MHz, CDCl$_3$) was as follows: δ=6.81 (1H, d, J=8.2); 6.60 (1H, d, J=8.2); 5.88 (1H, s, H-5); 4.43 (1H, d, J=1.8); 4.39 (2H, s, OCH$_2$CO$_2$); 3.79-3.75 (2H, m, OCH$_2$CH$_2$O); 3.62-3.57 (2H, m, OCH$_2$CH$_2$O); 3.46 (s, 3H); 3.38 (s, 3H, CH$_2$OCH$_3$); 3.05-2.99 (2H, m); 2.96-2.84 (1H, m); 2.63 (1H, dd); 2.39-2.22 (4H, m); 2.12 (1H, t); 1.98 (1H, dt); 1.94-1.77 (2H, m); 1.71 (1H, dd, J1=13.0, J2=2.5); 1.36 (3H, s, CH$_3$C), 1.32 (1H, dd, J1=13.2, J2=9.4); 1.13-1.01 (1H, m); 1.04 (9H, s, C(CH$_3$)$_3$); 0.86-0.75 (1H, m); 0.75-0.64 (1H, m); 0.55-0.44 (2H, m, c-Pr); 0.16-0.08 (2H, m, c-Pr).

4.8 Synthesis of ALL0015 (Buprenorphine 3,6,9,12-tetraoxamidecyl Carbonate)

The same procedure as for ALL00106, starting from tetraethylene glycol monomethyl ether (62.4 mg, 0.3 mmol), triphosgene (26.7 mg, 0.09 mmol), Buprenorphine hydrochloride (150 mg, 0.3 mmol) and triethylamine (60.6 mg, 0.6 mmol), afforded 107 mg (51%) of ALL00115 as a white sticky solid.

4.9 Synthesis of ALL00116 (Buprenorphine 3,6,9,12-tetraoxamidecanoyl Ester)

Buprenorphine hydrochloride (75.6 mg, 0.15 mmol) was suspended in dichloromethane (2 mL) followed by triethylamine (16.7 mg, 0.165 mmol). The mixture was stirred at ambient temperature for 5 min. 3,6,9,12-Tetraoxamidecanoic acid (43.3 mg, 0.195 mmol) in dichloromethane (1.75 mL) was added followed by 4-dimethylaminopyridine (1.8 mg, 0.015 mmol) and N—N'-dicyclohexylcarbodiimide (49.5 mg, 0.24 mmol). The mixture was stirred at ambient temperature overnight. The mixture was filtered, concentrated under a reduced pressure and chromatographed on silica gel with hexane-ethyl acetate (gradient 4:1, 2:1, 1:1, 0:1). Fractions containing the product were concentrated under a reduced pressure, dissolved in hexane with a few drops of ethyl acetate, filtered and concentrated again to afford ALL00116 (65.5 mg, 65%) as a colorless oil.

For ALL00116, the $^1$H NMR (400 MHz, CDCl$_3$) was as follows: δ=6.81 (1H, d, J=8.2); 6.61 (1H, d, J=8.2); 5.89 (1H, s, H-5); 4.43 (1H, d, J=1.8); 4.40 (2H, s, OCH$_2$CO$_2$); 3.80-3.76 (2H, m, PEG); 3.73-3.63 (8H, m, PEG); 3.57-3.53 (2H, m, PEG); 3.46 (s, 3H); 3.38 (s, 3H, CH$_2$OCH$_3$); 3.06-2.98 (2H, m); 2.94-2.84 (1H, m); 2.63 (1H, dd); 2.39-2.22 (4H, m); 2.12 (1H, t); 1.98 (1H, dt); 1.94-1.77 (2H, m); 1.71 (1H, dd, J1=13.0, J2=2.5); 1.36 (3H, s, CH$_3$C), 1.32 (1H, dd, J1=13.2, J2=9.4); 1.13-1.01 (1H, m); 1.04 (9H, s, C(CH$_3$)$_3$); 0.86-0.75 (1H, m); 0.75-0.64 (1H, m); 0.55-0.44 (2H, m, c-Pr); 0.16-0.08 (2H, m, c-Pr).

5.0 In Vitro Skin Permeation Studies 5.1 Preparation of Receiver Fluid 1

One liter of receiver fluid was prepared by measuring 1 L of nanopure water into a graduated cylinder. Ninety percent of the water was added to an Erlenmeyer flask. One bottle of Hanks' salts was added to the water along with 5.96 g of HEPES and 0.35 g of sodium bicarbonate. The pH of the solution was adjusted with 1 N sodium hydroxide solution to pH 7.4. The remaining water was added and the receiver fluid was filtered through a 0.2, filter (Millipore, Billerica, Mass.). Fifty milligrams of gentamicin was added to the filtered receiver fluid and 400 mL of the receiver fluid was removed and replaced with 400 mL of PEG 400.

5.2 Preparation of Receiver Fluid 2

One liter of receiver fluid was prepared by measuring 857 mL or 714 mL of nanopure water into a graduated cylinder. Ethanol (70%) was added (143 mL or 286 mL). The receiver fluid was filtered through a 0.2 µfilter (Millipore, Billerica, Mass.).

5.3 Preparation of the Formulations

Each compound was made up in 100% propylene glycol (PG). For the PG solution, approximately 25-35 mg of the appropriate compound was weighed into a glass culture tube. Propylene glycol was added to give about 102 mg/mL solution. For the gel formulation, the appropriate drug was weighed out (1% of the formulation). To the drug, absolute ethanol was added (92% of the formulation). The solution was vortexed and propylene glycol was added (5% of the formulation). The solution was vortexed and the gelling agent [Klucel® hydroxypropylcellulose] was added (2% of the formulation). Other formulations included propylene glycol/ethanol [96/4].

5.4 Permeation Experiments

Dermatomed skin harvested from abdominoplasty, stored at −20° C., was used for the experiments. A PermeGear flow-through (In-Line, Riegelsville, Pa.) diffusion cell system was used for the skin permeation studies.

Diffusion cells were kept at 32° C. with a circulating water bath. Human epidermal skin was arranged in the diffusion cell with stratum corneum (upper layer of skin) facing the donor compartment. The permeation area of the skin was 0.95 $cm^2$. Data was collected from a human skin donor with three to four diffusion cells per treatment.

Receiver solution was HEPES-buffered Hanks' balanced salts with gentamicin containing 40% PEG 400 at a pH of 7.4 or aqueous ethanol and flow rate was adjusted to 0.8 mL/h. Each cell was charged with 0.050 mL, 0.075 mL or 0.10 mL of the respective drug formulation (donor solution). The formulation was applied to ensure complete coverage. Diffusion cells were covered with a cap for the duration of the study.

Samples were collected into scintillation vials in 3 hour increments for 24 hours, except for the initial diffusion study which was conducted for 48 hours. All the samples were stored at 4° C. until extracted. An aliquot (0.5 mL) of the diffusion sample was placed into a HPLC vial and 0.5 mL of acetonitrile was added to the sample, capped and vortexed. For diffusion studies conducted with aqueous ethanol as the receiver fluid, 0.9 mL of the collected sample was placed into HPLC vials for analysis without dilution.

At the end of the experiment, the skin tissue was removed from the diffusion cell, rinsed with nanopure water, and blotted dry with a paper towel. The skin was tape stripped twice using book tape (Scotch™, 3M, St. Paul, Minn.) to remove drug formulation adhering to the tissue surface. The area of skin in contact with the drug was cut out, chopped up and placed in a pre-weighed scintillation vial. Ten mL of acetonitrile was added to the vial and drug was extracted from the skin by shaking at room temperature overnight. The following day a 1 mL aliquot was removed and added into a HPLC vial for analysis.

At the end of the experiment, a 0.01 mL aliquot of the PG donor solution was removed and added to a scintillation vial containing 10 mL of acetonitrile. The vials were vortexed and then sonicated for 15 min. An aliquot of 1 mL was removed and transferred into a HPLC vial for analysis.

6.0 Analytical Method

| | |
|---|---|
| Column | Brownlee ® $C_8$ reversed phase Spheri 5 µm, (4.6 × 220 mm) column with a Brownlee ® $C_8$ reversed phase 7 µm (3.2 × 150 mm) guard column |
| Mobile phase | 80:20 (acetonitrile:0.05% trifluroacetic acid with 5% acetonitrile), 80:20 (acetonitrile:0.10% trifluroacetic acid with 5% acetonitrile) or 70:30 (acetonitrile:0.10% trifluroacetic acid with 5% acetonitrile) |
| Flow rate | 1.5 mL/min |
| Wavelength | 210 or 220 nm |
| Injection volume | 100 µL (diffusion samples and respective standards) 20 µL (skin samples, donor samples, and respective standards) |
| Run time | 6-18 min |
| Retention times | buprenorphine = 4.3, 4.5, 5.0, or 9.1 min ALL00106 = 6.0, 7.2-7.4 or 14.2 min ALL00107 = 5.5, 5.7, 7.5, or 11.2 min ALL00108 = 5.0-5.2 or 5.7 min ALL00110 = 3.6 min ALL00113 = 5.1-5.2 min ALL00114 = 5.2 min ALL00115 = 5.3 min ALL00116 = 5.1 or 5.4 min |

7.0 Data Analysis

The cumulative quantity of drug collected in the receiver compartment was plotted as a function of time. The flux value for a given experiment was obtained from the slope of a steady state portion of the cumulative amount of drug permeated vs. time plot. Lag time was obtained from the x-intercept of the steady state portion of the cumulative amount of drug permeated vs. time plot. In the Tables, the combined results of the delivered prodrug and buprenorphine from the prodrug are listed as "total buprenorphine". These values represent the data as total buprenorphine equivalents delivered in the form of buprenorphine and/or prodrug.

Section III

Results

Originally the Hanks' buffer was used for the receiver fluid; however, the receiver fluid was changed to the aqueous ethanol to improve the sensitivity of the HPLC assay. With the Hanks' buffer, ALL00106 and ALL00107 permeated through the human skin as buprenorphine. Intact prodrug was found in the diffusion samples for ALL00106 but it was only for the initial 3 h sample or it was below the limit of detection after the initial sample. Both buprenorphine and intact prodrug were found in the skin samples. ALL00106 and ALL00107 had higher total buprenorphine in the skin compared to buprenorphine base. A lower flux enhancement was seen with ALL00106 or ALL00107. With the aqueous ethanol buffer, ALL00107 and ALL00108 permeated through the skin as buprenorphine and intact prodrug. Intact prodrug and buprenorphine were also found in the skin samples. ALL00108 had a flux enhancement of 2.35 relative to the buprenorphine base and a cumulative amount (nmol) 4× higher than the buprenorphine base.

In Table 8, ALL00108 had a flux enhancement compared to the parent compound with the gel formulation. ALL00107 and ALL00108 also had higher cumulative amount of total drug (nmol) at the end of the 24 h study compared to buprenorphine base. In Table 10, ALL00114 and ALL00115 both had improved flux values compared to the parent drug and had higher cumulative amount of total drug (nmol) at the end of the 24 h study. There appeared to be some depletion of drug with the gel formulation studies toward the last couple of time points but this would be improved by adding more drug/gel formulation.

In Table 9 and 11 with the propylene glycol donor solution, ALL0016, ALL00108, ALL00110, ALL00114, and ALL00115 all had flux enhancements compared to the parent compound. The five prodrugs also had higher cumulative amounts at the end of the study compared to the parent compound.

With both the gel formulation and propylene glycol, ALL00115 was mostly detected as intact prodrug in the receiver fluid with only trace amounts of the parent compound. For the remainder of the prodrugs, they were primarily detected as the parent drug in receiver fluid.

ALL00116 had a flux enhancement of 9.2 over the parent compound, buprenorphine base. The flux values of buprenorphine base was $0.3 \pm 0.2$ nmol/cm$^2$/h and the total buprenorphine from ALL00116 was $2.7 \pm 0.7$ nmol/cm$^2$/h. The cumulative amount of drug (nmol) for buprenorphine base was $3.4 \pm 2.8$ compared to total buprenorphine from ALL00116 which was $30.4 \pm 7.0$. Skin concentrations for buprenorphine base were $1.1 \pm 0.6$ µmol/g compared to total buprenorphine from ALL00116 which was $22.7 \pm 6.8$.

The graphs show the cumulative amount (nmol) of parent/prodrug permeated over the 24 h study period.

Section IV

Tables

TABLE 1

Buprenorphine and buprenorphine prodrugs

| Compound | Molecular formula | Molecular weight | Melting point |
|---|---|---|---|
| buprenorphine | C$_{29}$H$_{41}$NO$_4$ | 467.64 | 212-215° C. |
| ALL00106 | C$_{37}$H$_{55}$NO$_9$ | 657.83 | — |
| ALL00107 | C$_{31}$H$_{43}$NO$_6$ | 525.68 | 184-188° C. |
| ALL00108 | C$_{36}$H$_{53}$NO$_8$ | 627.81 | 195-198° C. |
| ALL00110 | C$_{34}$H$_{49}$NO$_8$ | 599.75 | — |

Table 1 shows the molecular formula, molecular weight and some melting points for several compounds including buprenorphine and four prodrugs of buprenorphine identified as ALL00106, ALL00107, ALL00108 and ALL00109. The molecular structure for each of these buprenorphine prodrugs is shown in as Formulas II-V.

TABLE 2

Permeation data of buprenorphine (n = 3) in propylene glycol

| Compound | 24 h skin conc (µmol/g) | 24 h cumulative amt (nmol) | 48 h cumulative amt (nmol) | Flux (nmol/cm$^2$/h) | Lag time (h) |
|---|---|---|---|---|---|
| buprenorphine | $1.1 \pm 0.2$ | $18.9 \pm 8.0$ | $35.3 \pm 8.7$ | $0.70 \pm 0.06$ | $5.7 \pm 0.0$ |

Table 2 shows the in vitro permeation of buprenorphine in a propylene glycol carrier. The data in Table 2 provides the 24 h skin concentration in µmol of buprenorphine per gram of skin, the 24 h and 48 h cumulative amount of buprenorphine which has permeated the skin sample (nmol), the buprenorphine flux in units of nmol/cm$^2$/h and the lag time in hours. The flux is a measure of the amount of substance (buprenorphine in Table 2) to pass through a predetermined area (1 cm$^2$ in Table 2) per unit time. The lag time is a measure of the length of time for a drug to establish a uniform concentration gradient in the skin.

TABLE 3

Permeation data of buprenorphine (n = 3), ALL00106 (n = 4), and ALL00107 (n = 3) in propylene glycol

| Compound | 24 h skin conc* (µmol/g) | 24 h cumulative amt (nmol) | Flux (nmol/cm$^2$/h) | Flux enhancement | Lag time (h) |
|---|---|---|---|---|---|
| buprenorphine | $0.7 \pm 0.4$ | $9.8 \pm 1.4$ | $0.45 \pm 0.04$ | — | $2.0 \pm 1.4$ |
| ALL00106 | $0.2 \pm 0.1$ (Bup) $2.1 \pm 1.5$ (PD) | $11.4 \pm 0.8$ | $0.54 \pm 0.07$ | 1.20 | NA |
| ALL00107 | $0.1 \pm 0.0$ (Bup) $1.6 \pm 0.7$ (PD) | $11.5 \pm 1.8$ | $0.53 \pm 0.07$ | 1.18 | $0.4 \pm 0.2$ |

*In the skin of prodrug treated cells, both intact prodrug and the parent drug was measured Table 3 shows the in vitro permeation of buprenorphine and buprenorphine prodrugs in a propylene glycol carrier. The data in Table 3 provides the 24 h skin concentration in µmol of buprenorphine and prodrug (if administered) per gram of skin, the 24 h cumulative amount of buprenorphine which has permeated the skin sample (nmol), the total buprenorphine flux in units of nmol/cm$^2$/h, the flux enhancement and the lag time in hours. The flux enhancement values of 1.20 for ALL00106 ($0.54 \pm 0.07/0.45 \pm 0.04$) and 1.18 ($0.53 \pm 0.07/0.45 \pm 0.04$) for ALL00107 show the increase in flux for buprenorphine prodrugs ALL00106 and ALL00107 relative to flux for buprenorphine. Also shown in Table 3 is an increase in both the 24 h skin concentration (µmol/g) and the 24 h cumulative amount (nmol) of buprenorphine prodrugs ALL00106 and ALL00107 relative to that of buprenolphine.

TABLE 4

Permeation data of buprenorphine (n = 3) in propylene glycol (10% aq. ethanol receiver fluid)

| Compound | 24 h skin conc (µmol/g) | 24 h cumulative amt (nmol) | Flux (nmol/cm$^2$/h) | Lag time (h) |
|---|---|---|---|---|
| buprenorphine | $0.3 \pm 0.2$ | $0.6 \pm 0.2$ | $0.08 \pm 0.02$ | $16.8 \pm 0.2$ |

Table 4 shows the in vitro permeation of buprenorphine in a propylene glycol carrier with a 10% aqueous ethanol receiver fluid. The data in Table 4 provides the 24 h skin concentration in μmol of buprenoiphine per gram of skin, the 24 h cumulative amount of buprenorphine which has permeated the skin sample (nmol), the buprenorphine flux in units of nmol/cm$^2$/h and the lag time in hours. The flux and lag time have the meaning as set forth with respect to Table 2.

TABLE 5

Permeation data of buprenorphine (n = 3) in propylene glycol (25% aq. ethanol receiver fluid)

| Compound | 24 h skin conc (μmol/g) | 24 h cumulative amt (nmol) | Flux (nmol/cm$^2$/h) | Lag time (h) |
|---|---|---|---|---|
| buprenorphine | 0.5 ± 0.1 | 0.7 ± 0.2 | 0.08 ± 0.03 | 13.6 ± 2.5 |

Table 5 shows the in vitro permeation of buprenorphine in a propylene glycol carrier with a 25% aqueous ethanol receiver fluid. The data in Table 5 provides the 24 h skin concentration in μmol of buprenorphine per gram of skin, the 24 h cumulative amount of buprenorphine which has permeated the skin sample (nmol), the buprenorphine flux in units of nmol/cm$^2$/h and the lag time in hours. The flux and lag time have the meaning as set forth with respect to Table 2.

(nmol), the buprenorphine flux in units of nmol/cm$^2$/h, the flux enhancement and the lag time in hours. The flux enhancement values of 0.40 for ALL00107 (0.17±0.06/0.43±0.03) and 2.35 (1.01±0.07/0.43±0.03) for ALL00108 show the increase in flux for buprenorphine prodrug ALL00108 relative to flux for buprenorphine while the flux decreases for ALL00107 relative to buprenorphine as the flux enhancement is less than one. Also shown in Table 6 is an increase in both the 24 h skin concentration (μmol/g) and the 24 h cumulative amount (nmol) of buprenorphine prodrug ALL00108 relative to that of buprenorphine.

TABLE 7

Additional buprenorphine prodrugs

| Compound | Molecular formula | Molecular weight |
|---|---|---|
| ALL00113 | $C_{35}H_{51}NO_8$ | 613.78 |
| ALL00114 | $C_{34}H_{49}NO_7$ | 583.76 |
| ALL00115 | $C_{39}H_{59}NO_{10}$ | 701.89 |
| ALL00116 | $C_{38}H_{57}NO_9$ | 671.86 |

TABLE 6

Permeation data of buprenorphine (n = 2), ALL00107 (n = 3), and ALL00108 (n = 2) in propylene glycol (25% aq. ethanol receiver fluid)

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 0.4 ± 0.1 | 4.2 ± 0.6 | 0.43 ± 0.03 | — | 14.0 ± 0.9 |
| Total buprenorphine (ALL00107) | 2.0 ± 0.7 | 1.5 ± 0.8 | 0.17 ± 0.06 | 0.40 | 15.0 ± 1.2 |
| Buprenorphine from ALL00107 | 0.1 ± 0.0 | 0.6 ± 0.0 | 0.06 ± 0.00 | | 13.0 ± 0.4 |
| ALL00107 | 1.9 ± 0.7 | 0.9 ± 0.8 | — | | — |
| Total buprenorphine (ALL00108) | 1.4 ± 0.4 | 17.3 ± 1.6 | 1.01 ± 0.07 | 2.35 | 6.0 ± 0.5 |
| Buprenorphine from ALL00108 | 0.4 ± 0.1 | 9.7 ± 0.4 | 0.90 ± 0.07 | | 12.5 ± 1.3 |
| ALL00108 | 1.0 ± 0.3 | 7.6 ± 2.0 | — | | — |

* total buprenorphine = total buprenorphine equivalents delivered in the form of buprenorphine and/or prodrug Table 6 shows the in vitro permeation of buprenorphine in a propylene glycol carrier with a 25% aqueous ethanol receiver fluid. The data in Table 6 provides the 24 h skin concentration in μmol of buprenorphine and prodrug (if administered) per gram of skin, the 24 h cumulative amount of buprenorphine which has permeated the skin sample Table 7 shows the molecular formula and molecular weight for four prodrugs of buprenorphine identified as ALL00113, ALL00114, ALL00115 and ALL00116. The molecular structure for each of these buprenorphine prodrugs is shown in as Formulas VI-IX.

TABLE 8

Permeation data of buprenorphine (n = 2), ALL00106 (n = 3), ALL00107 (n = 3), and ALL00108 (n = 3) in gel formulation

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 6.3 ± 1.3 | 12.4 ± 3.1 | 0.9 ± 0.2 | — | 3.3 ± 0.6 |
| Total buprenorphine (ALL00106) | 12.2 ± 3.6 | 5.5 ± 0.5 | 0.4 ± 0.1 | 0.4 | 6.5 ± 1.1 |
| Buprenorphine from ALL00106 | 0.3 ± 0.1 | 1.7 ± 0.3 | 0.2 ± 0.1 | | 4.7 ± 1.5 |
| ALL00106 | 11.9 ± 3.6 | 3.8 ± 0.3 | 0.3 ± 0.0 | | 8.2 ± 0.8 |
| Total buprenorphine (ALL00107) | 4.1 ± 0.4 | 16.9 ± 2.6 | 0.8 ± 0.2 | 0.9 | 6.7 ± 0.0 |
| Buprenorphine from ALL00107 | 0.5 ± 0.0 | 2.7 ± 0.5 | 0.1 ± 0.0 | | 5.1 ± 0.0 |
| ALL00107 | 4.0 ± 0.1 | 14.2 ± 2.4 | 0.7 ± 0.1 | | 3.5 ± 4.8 |
| Total buprenorphine (ALL00108) | 2.2 ± 1.8 | 21.0 ± 6.7 | 1.2 ± 0.6 | 1.3 | 7.8 ± 0.8 |
| Buprenorphine from ALL00108 | 0.2 ± 0.2 | 21.0 ± 6.7 | 1.2 ± 0.6 | | 7.8 ± 0.8 |
| ALL00108 | 1.9 ± 1.6 | — | — | | — |

* total buprenorphine = total buprenorphine equivalents delivered in the form of buprenorphine and/or prodrug Table 8 shows the in vitro permeation of buprenorphine and buprenorphine prodrugs in a gel formulation. The data in Table 8 provides the 24 h skin concentration in μmol of buprenorphine and prodrug (if administered) per gram of skin, the 24 h cumulative amount of buprenorphine which has permeated the skin sample (nmol), the total buprenorphine flux in units of nmol/cm$^2$/h, the flux enhancement and the lag time in hours. The flux enhancement value of 1.3 for ALL00108 (1.2±0.6/0.9±0.2) shows the increase in flux for buprenorphine prodrug ALL00108 relative to flux for buprenorphine. Also shown in Table 8 is an increase in the 24 h skin concentration (μmol/g) of total buprenorphine for buprenorphine prodrug ALL00106 and the 24 h cumulative amount (nmol) of total buprenorphine for buprenorphine prodrugs ALL00107 and ALL00108 relative to that of buprenorphine.

Table 10 shows the in vitro permeation of buprenorphine and buprenorphine prodrugs in a gel formulation. The data in Table 10 provides the 24 h skin concentration in μmol of buprenorphine and prodrug (if administered) per gram of skin, the 24 h cumulative amount of buprenorphine which has permeated the skin sample (nmol), the total buprenorphine flux in units of nmol/cm$^2$/h, the flux enhancement and the lag time in hours. The flux enhancement value of 2.5 for ALL00114 (0.5±0.2/0.2±0.0) and 1.2 for ALL00115 (0.2±0.1/0.2±0.0) shows the increase in flux for buprenorphine prodrugs ALL00114 and ALL00115 relative to flux for buprenorphine. Also shown in Table 10 is an increase in the 24 h cumulative amount (nmol) of total buprenorphine for buprenorphine prodrugs ALL00114 and ALL00115 relative to that of buprenorphine.

TABLE 9

Permeation data of buprenorphine (n = 3), ALL00106 (n = 3), and ALL00110 (n = 2) in propylene glycol

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 1.6 ± 1.6 | 15.9 ± 2.3 | 1.2 ± 0.2 | — | 11.4 ± 1.5 |
| Total buprenorphine (ALL00106) | 11.9 ± 4.4 | 48.9 ± 17.6 | 3.8 ± 1.1 | 3.2 | 10.6 ± 1.3 |
| Buprenorphine from ALL00106 | 1.6 ± 0.4 | 30.1 ± 13.2 | 2.3 ± 0.8 | | 10.2 ± 1.4 |
| ALL00106 | 10.4 ± 4.0 | 18.8 ± 4.6 | 1.5 ± 0.3 | | 11.1 ± 1.2 |
| Total buprenorphine (ALL00110) | 14.1 ± 3.2 | 27.0 ± 2.4 | 2.4 ± 0.3 | 2.0 | 11.9 ± 2.7 |
| Buprenorphine from ALL00110 | 2.5 ± 0.4 | 27.0 ± 2.4 | 2.4 ± 0.3 | | 11.9 ± 2.7 |
| ALL00110 | 11.6 ± 2.8 | — | — | | — |

* total buprenorphine = total buprenorphine equivalents delivered in the form of buprenorphine and/or prodrug Table 9 shows the in vitro permeation of buprenorphine and buprenorphine prodrugs in a propylene glycol carrier. The data in Table 9 provides the 24 h skin concentration in μmol of buprenorphine and prodrug (if administered) per gram of skin, the 24 h cumulative amount of buprenorphine which has permeated the skin sample (nmol), the total buprenorphine flux in units of nmol/cm$^2$/h, the flux enhancement and the lag time in hours. The flux enhancement value of 3.2 for ALL00106 (3.8÷1.1/1.2±0.2) and 2.0 for ALL00110 (2.4±0.3/1.2±0.2) shows the increase in flux for buprenorphine prodrugs ALL00106 and ALL00110 relative to flux for buprenorphine. Also shown in Table 9 is an increase in the 24 h skin concentration (μmol/g) and the 24 h cumulative amount (nmol) of total buprenorphine for buprenorphine prodrugs ALL00106 and ALL00110 relative to that of buprenorphine.

TABLE 10

Permeation data of buprenorphine (n = 3), ALL00110 (n = 3), ALL00114 (n = 3), and ALL00115 (n = 2) in gel formulation

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 8.3 ± 4.0 | 2.5 ± 1.0 | 0.2 ± 0.0 | — | 6.0 ± 1.8 |
| Total buprenorphine (ALL00110) | 7.8 ± 7.5 | 1.9 ± 1.0 | 0.1 ± 0.1 | 0.7 | 12.4 ± 4.1 |
| Buprenorphine from ALL00110 | 0.7 ± 0.6 | 1.9 ± 1.0 | 0.1 ± 0.1 | | 12.4 ± 4.1 |
| ALL00110 | 7.1 ± 6.9 | — | — | | — |
| Total buprenorphine (ALL00114) | 7.4 ± 2.8 | 6.3 ± 1.7 | 0.5 ± 0.2 | 2.5 | 11.3 ± 5.8 |
| Buprenorphine from ALL00114 | 0.2 ± 0.1 | 6.3 ± 1.7 | 0.5 ± 0.2 | | 11.3 ± 5.8 |
| ALL00114 | 7.1 ± 2.8 | — | — | | — |
| Total buprenorphine (ALL00115) | 1.4 ± 0.4 | 4.5 ± 1.3 | 0.2 ± 0.1 | 1.2 | 7.6 ± 0.5 |
| Buprenorphine from ALL00115 | 0.1 ± 0.0 | TA | — | | — |
| ALL00115 | 3.4 ± 0.6 | 4.5 ± 1.3 | 0.2 ± 0.1 | | 7.6 ± 0.5 |

* total buprenorphine = total buprenorphine equivalents delivered in the form of buprenorphine and/or prodrug

TABLE 11

Permeation data of buprenorphine (n = 3), ALL00108 (n = 2), ALL00114 (n = 2), and ALL00115 (n = 2) in propylene glycol

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 1.1 ± 0.1 | 3.0 ± 0.7 | 0.3 ± 0.1 | — | 13.8 ± 0.8 |
| Total buprenorphine (ALL00108) | 2.4 ± 0.7 | 5.8 ± 0.7 | 0.5 ± 0.0 | 1.7 | 10.9 ± 2.4 |
| Buprenorphine from ALL00108 | ND | 5.8 ± 0.7 | 0.5 ± 0.0 | | 10.9 ± 2.4 |
| ALL00108 | 2.4 ± 0.7 | — | — | | — |
| Total buprenorphine (ALL00114) | 20.0 ± 0.9 | 8.8 ± 0.0 | 0.9 ± 0.1 | 3.0 | 13.2 ± 0.9 |
| Buprenorphine from ALL00114 | 0.9 ± 0.0 | 8.8 ± 0.0 | 0.9 ± 0.1 | | 13.2 ± 0.9 |
| ALL00114 | 19.1 ± 0.9 | — | — | | — |
| Total buprenorphine (ALL00115) | 0.8 ± 0.2 | 6.0 ± 1.3 | 0.7 ± 0.2 | 2.3 | 9.4 ± 8.5 |
| Buprenorphine from ALL00115 | ND | TA | — | | — |
| ALL00115 | 0.8 ± 0.2 | 6.0 ± 1.3 | — | | — |

* total buprenorphine = total buprenorphine equivalents delivered in the form of buprenorphine and/or prodrug Table 11 shows the in vitro permeation of buprenorphine and buprenorphine prodrugs in a propylene glycol carrier. The data in Table 11 provides the 24 h skin concentration in μmol of buprenorphine and prodrug (if administered) per gram of skin, the 24 h cumulative amount of buprenorphine which has permeated the skin sample (nmol), the total buprenorphine flux in units of nmol/cm$^2$/h, the flux enhancement and the lag time in hours. The flux enhancement value of 1.7 for ALL00108 (0.5±0.0/0.3±0.1), 3.0 for ALL00114 (0.9±0.1/0.3±0.1) and 2.3 for ALL00115 (0.7±0.2/0.3±0.1) shows the increase in flux for buprenorphine prodrugs ALL00108, ALL00114 and ALL00115 relative to flux for buprenorphine. Also shown in Table 11 is an increase in the 24 h skin concentration (μmol/g) for buprenorphine prodrugs ALL00108 and ALL00114 and the 24 h cumulative amount (nmol) of total buprenorphine for buprenorphine prodrugs ALL00108, ALL00114 and ALL00115 relative to that of buprenorphine.

Table 12 shows the in vitro permeation of buprenorphine and a buprenorphine prodrug in a propylene glycolethanol [96/4] carrier. The data in Table 12 provides the 24 h skin concentration in μmol of buprenorphine and prodrug (if administered) per gram of skin, the 24 h cumulative amount of buprenorphine which has permeated the skin sample (nmol), the total buprenorphine flux in units of nmol/cm$^2$/h, the flux enhancement and the lag time in hours. The flux enhancement value of 9.2 for ALL00116 (2.7±0.7/0.3±0.2) shows the increase in flux for buprenorphine prodrug ALL00116 relative to flux for buprenorphine. Also shown in Table 11 is an increase in the 24 h skin concentration (μmol/g) and the 24 h cumulative amount (nmol) of total buprenorphine for buprenorphine prodrug ALL00116 relative to that of buprenorphine.

TABLE 12

Permeation data of buprenorphine (n = 3) and ALL00116 (n = 3) in propylene glycol/ethanol [96:4]

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 1.1 ± 0.6 | 3.4 ± 2.8 | 0.3 ± 0.2 | — | 12.5 ± 2.1 |
| Total buprenorphine (ALL00116) | 22.7 ± 6.8 | 30.4 ± 7.0 | 2.7 ± 0.7 | 9.2 | 12.3 ± 1.2 |
| Buprenorphine from ALL00116 | 2.4 ± 0.9 | 8.7 ± 1.2 | 0.8 ± 0.2 | | 13.2 ± 0.8 |
| ALL00116 | 20.4 ± 5.8 | 21.7 ± 6.7 | 1.9 ± 0.6 | | 11.8 ± 1.4 |

* total buprenorphine = total buprenorphine equivalents delivered in the form of buprenorphine and/or prodrug

TABLE 13

Permeation data of buprenorphine (n = 2), ALL00113 (n = 3), and ALL00116 (n = 3) in gel formulation

| Compound | 24 h skin conc (μmol/g) | 24 h cumulative amt (nmol) | Flux (nmol/cm$^2$/h) | Flux enhancement | Lag time (h) |
|---|---|---|---|---|---|
| buprenorphine | 10.7 ± 5.3 | 3.5 ± 1.8 | 0.4 ± 0.1 | — | 3.6 ± 1.3 |
| Total buprenorphine (ALL00113) | 0.9 ± 0.2 | 0.9 ± 0.2 | 0.05 ± 0.01 | 0.1 | 7.9 ± 0.9 |
| Buprenorphine from ALL00113 | 0.1 ± 0.1 | 0.9 ± 0.2 | 0.05 ± 0.01 | | 7.9 ± 0.9 |
| ALL00113 | 0.8 ± 0.1 | — | — | | — |
| Total buprenorphine (ALL00116) | 3.5 ± 0.9 | 5.5 ± 0.6 | 0.4 ± 0.1 | 1.2 | 7.2 ± 0.6 |
| Buprenorphine from ALL00116 | 0.2 ± 0.0 | 5.5 ± 0.6 | 0.4 ± 0.1 | | 7.2 ± 0.6 |
| ALL00116 | 3.3 ± 0.8 | — | — | | — |

* total buprenorphine = total buprenorphine equivalents delivered in the form of buprenorphine and/or prodrug Table 13 shows the in vitro permeation of buprenorphine and a buprenorphine prodrugs in a gel formulation. The data in Table 13 provides the 24 h skin concentration in μmol of buprenorphine and prodrug (if administered) per gram of skin, the 24 h cumulative amount of buprenorphine which has permeated the skin sample (nmol), the total buprenorphine flux in units of nmol/cm²/h, the flux enhancement and the lag time in hours. The flux enhancement value of 1.2 for ALL00116 (0.4±0.1/0.4±0.1) shows the increase in flux for buprenorphine prodrug ALL00116 relative to flux for buprenorphine. Also shown in Table 12 is an increase in the 24 h cumulative amount (nmol) of total buprenorphine for buprenorphine prodrug ALL00116 relative to that of buprenorphine.

All references, including printed publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of this disclosure (especially in the context of the following claims) are to be construed to cover both the singular and the plural, unless otherwise indicated herein or clearly contradicted by context. All methods and individual method steps described herein can be performed in any suitable order or simultaneously unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of rations that can be formed by, or derived from, any of the data disclosed herein represents further embodiments of the present disclosure and are included as a part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

We claim:

1. A compound having the formula:

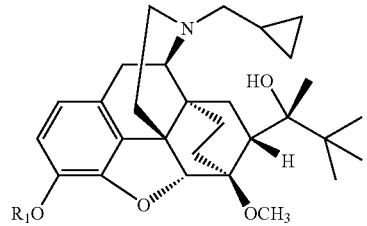

wherein $R_1$ is selected from the group consisting of oxygenated alkyl carbonate, and oxygenated ester, wherein the oxygenated ester does not terminate in an —OH group.

2. The compound of claim 1 wherein the oxygenated alkyl carbonate is a hydroxylated alkyl carbonate.

3. The compound of claim 1 wherein the oxygenated alkyl carbonate is an oxa-carbonate.

4. The compound of claim 3 wherein the oxa-carbonate is a pegylated carbonate.

5. The compound of claim 1 wherein the oxygenated ester is an oxa-ester.

6. The compound of claim 5 wherein the oxa-ester is pegylated ester.

7. A compound of claim 1 having an in vitro transdermal flux enhancement of greater than one relative to buprenorphine.

8. A compound of claim 1 having an in vitro transdermal flux (nmol/cm²/hr) greater than buprenorphine.

9. A compound of claim 1 having a twenty-four hour cumulative amount (nmol) of in vitro transdermal permeation greater than buprenorphine.

10. A pharmaceutical composition comprising:
    (a) a buprenorphine prodrug selected from the group consisting of a compound having the formula:

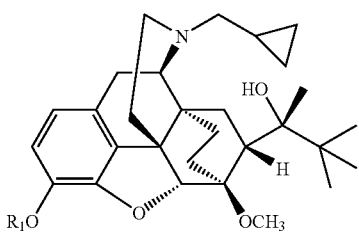

wherein $R_1$ is selected from the group consisting of oxygenated alkyl carbonate, and oxygenated ester, wherein the oxygenated ester does not terminate in an —OH group; and (b) a pharmaceutical excipient.

11. The pharmaceutical composition of claim 10 further comprising a second compound selected from the group consisting of: naltrexone and prodrugs of naltrexone.

12. The pharmaceutical composition of claim 10 further comprising a second compound having the formula:

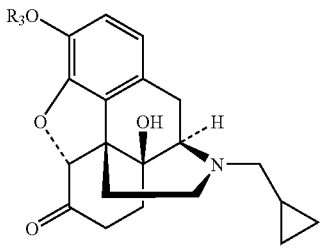

wherein $R_3$ is selected from the group consisting of: H; —COC(CH$_3$)$_3$; —COCH(CH$_3$)$_2$; —COCH$_2$CH(CH$_3$)$_2$; —COCH(CH$_2$CH$_3$)$_2$; —CON(CH$_2$CH$_3$)$_2$; —CON(CH(CH$_3$)$_2$)$_2$; —COOCH(CH$_3$)$_2$;

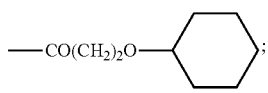

and —CO(CH$_2$)$_2$OCH$_3$.

13. The pharmaceutical composition of claim 10 further comprising a second compound selected from the group consisting of: 3-O-pivalyl naltrexone; 3-O-isovaleryl naltrexone; 3-O-(2'-ethylbutyryl) naltrexone; 3-O-isobutyryl naltrexone; 3-O-isopropyloxycarbonyl naltrexone; 3-O-tertiarybutyloxycarbonyl naltrexone; N,N-dimethyl-3-O-carbamate naltrexone; N,N-diethyl-3-O-carbamate naltrexone; and N,N-diisopropyl-3-O-carbamate naltrexone.

14. A method of treating a medical condition in a mammal selected from the group consisting of: opioid dependence, alcohol dependence and pain comprising the step of transdermally administering to the mammal a buprenorphine prodrug from the group consisting of:

a compound having the formula:

(I)

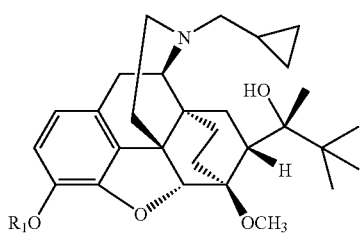

wherein $R_1$ is selected from the group consisting of oxygenated alkyl carbonate, and oxygenated ester, wherein the oxygenated ester does not terminate in an —OH group.

15. The method of claim 14 further comprising the step of transdermally administering to the mammal a second compound having the formula:

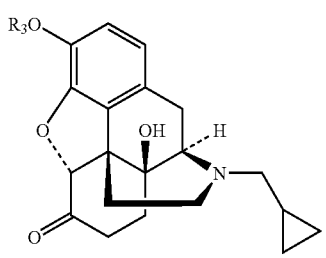

wherein $R_3$ is selected from the group consisting of: H; —COC(CH$_3$)$_3$; —COCH(CH$_3$)$_2$; —COCH$_2$CH(CH$_3$)$_2$; —COCH(CH$_2$CH$_3$)$_2$; —CON(CH$_2$CH$_3$)$_2$; —CON(CH(CH$_3$)$_2$)$_2$; —COOCH(CH$_3$)$_2$;

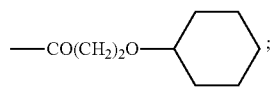

and —CO(CH$_2$)$_2$OCH$_3$.

16. The method of claim 14 further comprising the step of transdermally administering a second compound to the mammal selected from the group consisting of: naltrexone; 3-O-pivalyl naltrexone; 3-O-isovaleryl naltrexone; 3-O-(2'-ethylbutyryl) naltrexone; 3-O-isobutyryl naltrexone; 3-O-isopropyloxycarbonyl naltrexone; 3-O-tertiarybutyloxycarbonyl naltrexone; N,N-dimethyl-3-O-carbamate naltrexone; N,N-diethyl-3-O-carbamate naltrexone; and N,N-diisopropyl-3-O-carbamate naltrexone.

17. A method of transdermally administering a buprenorphine prodrug to a mammal comprising the steps of:
(a) obtaining a pharmaceutical composition comprising:
(i) a compound having the formula:

(I)

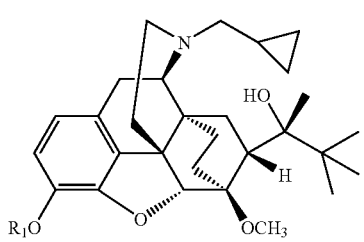

wherein $R_1$ is selected from the group consisting of oxygenated alkyl carbonate, and oxygenated ester, wherein the oxygenated ester does not terminate in an —OH group; and (ii) a pharmaceutically acceptable excipient; and (b) contacting the pharmaceutical composition with the skin of the mammal.

18. A method for transdermally delivering a buprenorphine prodrug to a mammal comprising the steps of:

(a) obtaining a pharmaceutical composition comprising:

(i) a compound having the formula:

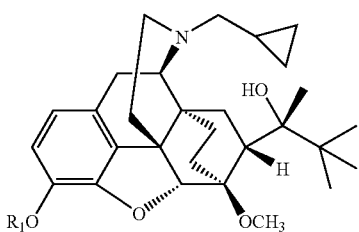

(I)

wherein $R_1$ is selected from the group consisting of oxygenated alkyl carbonate, and oxygenated ester, wherein the oxygenated ester does not terminate in an —OH group; and (ii) a naltrexone prodrug having the formula:

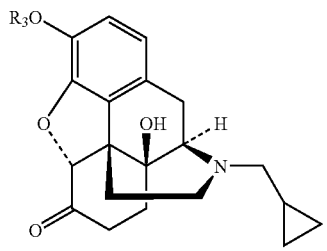

wherein $R_3$ is selected from the group consisting of:
H; —COC(CH$_3$)$_3$; —COCH(CH$_3$)$_2$;
—COCH$_2$CH(CH$_3$)$_2$; —COCH(CH$_2$CH$_3$)$_2$;
—CON(CH$_2$CH$_3$)$_2$; —CON(CH(CH$_3$)$_2$)$_2$;
—COOCH(CH$_3$)$_2$;

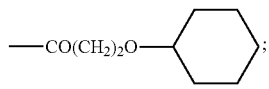

and —CO(CH$_2$)$_2$OCH$_3$; and (b) contacting the pharmaceutical composition with the skin of the mammal.

* * * * *